US008337434B2

(12) United States Patent
Vaezy et al.

(10) Patent No.: US 8,337,434 B2
(45) **Date of Patent: *Dec. 25, 2012**

(54) METHODS FOR USING HIGH INTENSITY FOCUSED ULTRASOUND AND ASSOCIATED SYSTEMS AND DEVICES

(75) Inventors: Shahram Vaezy, Seattle, WA (US); Arthur H. Chan, Plano, TX (US); Victor Y. Fujimoto, San Francisco, CA (US); Donald E. Moore, Seattle, WA (US); Roy W. Martin, Anacortes, WA (US)

(73) Assignee: University of Washington, Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/946,727

(22) Filed: Nov. 15, 2010

(65) Prior Publication Data

US 2011/0201929 A1 Aug. 18, 2011

Related U.S. Application Data

(60) Division of application No. 11/928,667, filed on Oct. 30, 2007, now Pat. No. 7,850,626, which is a division of application No. 10/977,339, filed on Oct. 29, 2004, now Pat. No. 7,520,856, and a continuation-in-part of application No. 10/770,350, filed on Feb. 2, 2004, now Pat. No. 7,686,763, which is a continuation-in-part of application No. 10/166,795, filed on Jun. 7, 2002, now Pat. No. 6,716,184, which is a division of application No. 09/397,471, filed on Sep. 17, 1999, now Pat. No. 6,425,867.

(60) Provisional application No. 60/516,099, filed on Oct. 31, 2003.

(51) Int. Cl.
*A61H 1/00* (2006.01)

(52) U.S. Cl. ............ 601/2; 600/439; 600/476; 600/478; 600/127; 600/459

(58) Field of Classification Search .................. 601/2-4; 600/476-478, 114, 127, 459
See application file for complete search history.

(56) References Cited

U.S. PATENT DOCUMENTS 385,256 A 6/1888 Eggers
(Continued)

FOREIGN PATENT DOCUMENTS

DE 04230415 3/1994
(Continued)

OTHER PUBLICATIONS

Aaslid et al., "Noninvasive transcranial Doppler ultrasound recording of flow velocity in basal cerebral arteries." *Journal of Neurosurgery*, vol. 57: 769-774, 1982.

(Continued)

*Primary Examiner* — Brian Casler
*Assistant Examiner* — Amanda Lauritzen
(74) *Attorney, Agent, or Firm* — Perkins Coie LLP

(57) ABSTRACT

A plurality of concepts related to HIFU therapy are disclosed, including a technique to spatially track and display the relative positions of a HIFU focal point and an imaging plane from an ultrasound imager, so that a clinician can ensure that the HIFU focus remains in the image plane during HIFU therapy, thereby facilitating image guided HIFU therapy. Also disclosed are a plurality of transvaginal probes that include a HIFU transducer optimized for the treatment of uterine fibroids. In one embodiment, the probe includes a piezoceramic crystal bonded to an aluminum lens, to achieve a HIFU transducer having a focal length of about 4 cm. In another embodiment, the probe includes a generally spoon-shaped transducer including a plurality of individual emitter elements. Still another concept disclosed herein is a method for evaluating a quality of a coupling between a liquid-filled volume encompassing a HIFU transducer and a tissue interface.

18 Claims, 17 Drawing Sheets

U.S. PATENT DOCUMENTS

| | | | | |
|---|---|---|---|---|
| 2,992,553 | A | 7/1961 | Joy | 73/644 |
| 4,059,098 | A | 11/1977 | Murdock | 73/644 |
| 4,484,569 | A | 11/1984 | Driller et al. | 128/60 |
| 4,545,386 | A | 10/1985 | Hetz et al. | 600/462 |
| 4,601,296 | A | 7/1986 | Yerushalmi | 607/156 |
| 4,688,578 | A | 8/1987 | Takano et al. | 600/459 |
| RE33,590 | E | 5/1991 | Dory | 128/999.999 |
| 5,039,774 | A | 8/1991 | Shikinami et al. | 528/60 |
| 5,065,742 | A | 11/1991 | Belikan et al. | 128/24 |
| 5,080,101 | A | 1/1992 | Dory | 128/999.999 |
| 5,080,102 | A | 1/1992 | Dory | 128/999.999 |
| 5,088,498 | A | 2/1992 | Beach et al. | 600/453 |
| 5,150,712 | A | 9/1992 | Dory | 128/999.999 |
| 5,170,790 | A | 12/1992 | Lacoste et al. | 600/437 |
| 5,178,148 | A | 1/1993 | Lacoste et al. | 600/439 |
| 5,183,046 | A | 2/1993 | Beach et al. | 600/453 |
| 5,215,680 | A | 6/1993 | D'Arrigo | 516/11 |
| 5,219,401 | A | 6/1993 | Cathignol et al. | 128/999.999 |
| 5,230,334 | A | 7/1993 | Klopotek | 128/999.999 |
| 5,289,820 | A | 3/1994 | Beach et al. | 600/443 |
| 5,311,869 | A | 5/1994 | Okazaki | 128/999.999 |
| 5,391,140 | A | 2/1995 | Schaetzle et al. | 601/4 |
| 5,394,877 | A | 3/1995 | Orr et al. | 600/459 |
| 5,471,988 | A | 12/1995 | Fujio et al. | 128/999.999 |
| 5,474,071 | A | 12/1995 | Chapelon et al. | 600/439 |
| 5,492,126 | A | 2/1996 | Hennige et al. | 600/439 |
| 5,507,790 | A | 4/1996 | Weiss | 607/100 |
| 5,520,188 | A | 5/1996 | Hennige et al. | 128/999.999 |
| 5,522,878 | A | 6/1996 | Montecalvo et al. | 607/152 |
| 5,526,815 | A | 6/1996 | Granz et al. | 128/999.999 |
| 5,536,489 | A | 7/1996 | Lohrmann et al. | 424/9.52 |
| 5,555,887 | A * | 9/1996 | Fraser et al. | 600/472 |
| 5,558,092 | A | 9/1996 | Unger et al. | 128/999.999 |
| 5,573,497 | A | 11/1996 | Chapelon | 601/2 |
| 5,609,485 | A | 3/1997 | Bergman et al. | 434/262 |
| 5,638,823 | A | 6/1997 | Akay et al. | 600/528 |
| 5,657,760 | A | 8/1997 | Ying et al. | 128/999.999 |
| 5,666,954 | A | 9/1997 | Chapelon et al. | 600/439 |
| 5,720,286 | A | 2/1998 | Chapelon et al. | 600/439 |
| 5,720,287 | A | 2/1998 | Chapelon et al. | 600/439 |
| 5,755,228 | A | 5/1998 | Wilson et al. | 600/459 |
| 5,762,066 | A | 6/1998 | Law et al. | 128/999.999 |
| 5,769,790 | A | 6/1998 | Watkins et al. | 600/439 |
| 5,807,285 | A | 9/1998 | Vaitekunas | 601/2 |
| 5,810,007 | A | 9/1998 | Holupka et al. | 600/439 |
| 5,817,021 | A | 10/1998 | Reichenberger | 600/439 |
| 5,823,962 | A | 10/1998 | Schaetzle et al. | 600/439 |
| 5,827,204 | A | 10/1998 | Grandia et al. | 601/2 |
| 5,833,647 | A | 11/1998 | Edwards | 604/22 |
| 5,840,028 | A | 11/1998 | Chubachi et al. | 600/437 |
| 5,846,517 | A | 12/1998 | Unger | 424/9.52 |
| 5,853,752 | A | 12/1998 | Unger et al. | 424/450 |
| 5,873,828 | A | 2/1999 | Fujio et al. | 600/439 |
| 5,879,314 | A | 3/1999 | Peterson et al. | 601/2 |
| 5,882,302 | A | 3/1999 | Driscoll, Jr. et al. | 600/371 |
| 5,895,356 | A | 4/1999 | Andrus et al. | 600/439 |
| 5,897,495 | A | 4/1999 | Aida et al. | 600/411 |
| 5,906,580 | A | 5/1999 | Kline-Schoder et al. | 600/459 |
| 5,919,139 | A | 7/1999 | Lin | 600/443 |
| 5,922,945 | A | 7/1999 | Allmaras et al. | 73/52 |
| 5,931,786 | A | 8/1999 | Whitmore, III et al. | 600/459 |
| 5,951,476 | A | 9/1999 | Beach | 600/437 |
| 5,976,092 | A | 11/1999 | Chinn | 600/459 |
| 5,993,389 | A | 11/1999 | Driscoll, Jr. et al. | 600/371 |
| 5,997,481 | A | 12/1999 | Adams et al. | 600/459 |
| 6,007,499 | A | 12/1999 | Martin et al. | 601/3 |
| 6,036,650 | A | 3/2000 | Wu et al. | 600/462 |
| 6,039,694 | A | 3/2000 | Larson et al. | 600/459 |
| 6,050,943 | A | 4/2000 | Slayton et al. | 600/439 |
| 6,067,371 | A | 5/2000 | Gouge et al. | 382/128 |
| 6,071,239 | A | 6/2000 | Cribbs et al. | 600/439 |
| 6,128,522 | A | 10/2000 | Acker et al. | 600/411 |
| 6,179,831 | B1 | 1/2001 | Bliweis | 606/21 |
| 6,221,015 | B1 | 4/2001 | Yock | 600/439 |
| 6,267,734 | B1 | 7/2001 | Ishibashi et al. | 601/2 |
| 6,409,720 | B1 | 6/2002 | Hissong et al. | 606/27 |
| 6,425,867 | B1 | 7/2002 | Vaezy et al. | 600/439 |
| 6,443,894 | B1 | 9/2002 | Sumanaweera et al. | 600/443 |
| 6,488,639 | B1 | 12/2002 | Ribault et al. | 601/2 |
| 6,491,672 | B2 | 12/2002 | Slepian et al. | 604/267 |
| 6,548,047 | B1 | 4/2003 | Unger | 424/9.51 |
| 6,551,576 | B1 | 4/2003 | Unger et al. | 424/9.52 |
| 6,584,360 | B2 | 6/2003 | Francischelli et al. | 607/98 |
| 6,595,934 | B1 | 7/2003 | Hissong et al. | 601/3 |
| 6,599,256 | B1 | 7/2003 | Acker et al. | 601/2 |
| 6,626,855 | B1 | 9/2003 | Weng et al. | 601/3 |
| 6,633,658 | B1 | 10/2003 | Dabney et al. | 382/128 |
| 6,656,136 | B1 | 12/2003 | Weng et al. | 601/2 |
| 6,676,601 | B1 | 1/2004 | Lacoste et al. | 600/439 |
| 6,685,639 | B1 | 2/2004 | Wang et al. | 600/439 |
| 6,709,407 | B2 | 3/2004 | Fatemi | 600/559 |
| 6,716,184 | B2 | 4/2004 | Vaezy et al. | 601/3 |
| 6,719,694 | B2 | 4/2004 | Weng et al. | 600/439 |
| 6,719,699 | B2 | 4/2004 | Smith | 600/459 |
| 6,726,627 | B1 | 4/2004 | Lizzi et al. | 600/439 |
| 6,735,461 | B2 | 5/2004 | Vitek et al. | 600/411 |
| 6,764,488 | B1 | 7/2004 | Burbank et al. | 606/51 |
| 6,846,291 | B2 | 1/2005 | Smith et al. | 600/459 |
| 6,875,176 | B2 | 4/2005 | Mourad et al. | 600/442 |
| 6,875,420 | B1 | 4/2005 | Quay | 424/9.52 |
| 6,905,498 | B2 | 6/2005 | Hooven | 606/50 |
| 6,932,771 | B2 | 8/2005 | Whitmore et al. | 607/105 |
| 6,955,648 | B2 | 10/2005 | Mozayeni et al. | 600/454 |
| 7,022,077 | B2 | 4/2006 | Mourad et al. | 600/442 |
| 7,052,463 | B2 | 5/2006 | Peszynski et al. | 600/459 |
| 7,285,093 | B2 | 10/2007 | Anisimov et al. | 600/437 |
| 7,445,599 | B2 | 11/2008 | Kelly et al. | 600/437 |
| 7,470,241 | B2 | 12/2008 | Weng et al. | 601/3 |
| 7,534,209 | B2 | 5/2009 | Abend | 600/437 |
| 7,628,764 | B2 | 12/2009 | Duarte et al. | 601/2 |
| 7,684,865 | B2 | 3/2010 | Aldrich et al. | 607/40 |
| 7,697,972 | B2 | 4/2010 | Verard et al. | 600/424 |
| 2002/0193831 | A1 | 12/2002 | Smith, III | 607/5 |
| 2003/0018255 | A1 | 1/2003 | Martin et al. | 600/3 |
| 2003/0069569 | A1 | 4/2003 | Burdette et al. | 600/427 |
| 2003/0195420 | A1 | 10/2003 | Mendlein et al. | 600/459 |
| 2004/0002654 | A1 | 1/2004 | Davidson et al. | 600/454 |
| 2004/0078034 | A1 | 4/2004 | Acker et al. | 606/27 |
| 2004/0097840 | A1 | 5/2004 | Holmer | 601/2 |
| 2004/0122493 | A1 | 6/2004 | Ishibashi et al. | 600/437 |
| 2004/0153126 | A1 | 8/2004 | Okai | 606/27 |
| 2004/0234453 | A1 | 11/2004 | Smith | 424/9.5 |
| 2004/0254620 | A1 | 12/2004 | Lacoste et al. | 607/96 |
| 2005/0065436 | A1 | 3/2005 | Ho et al. | 600/431 |
| 2005/0240102 | A1 | 10/2005 | Rachlin et al. | 600/459 |
| 2006/0184069 | A1 | 8/2006 | Vaitekunas | 601/2 |
| 2008/0045864 | A1 | 2/2008 | Candy et al. | 601/2 |
| 2008/0045865 | A1 | 2/2008 | Kislev | 601/3 |
| 2008/0200815 | A1 | 8/2008 | Van Der Steen et al. | 600/467 |
| 2008/0319375 | A1 | 12/2008 | Hardy | 604/22 |

FOREIGN PATENT DOCUMENTS

| | | |
|---|---|---|
| EP | 0 420 758 | 4/1991 |
| EP | 1 265 223 | 12/2002 |
| JP | H09-103434 | 4/1997 |
| JP | 2002-500939 | 1/2002 |
| JP | 2004-113789 | 4/2004 |
| WO | WO 97/31364 | 8/1997 |
| WO | WO 00/72919 | 12/2000 |
| WO | WO 02/069805 | 9/2002 |

OTHER PUBLICATIONS

Accord et al., "The Issue of Transmurality in Surgical Ablation for Atrial Fibrillation." *Cardiothoracic Surgery Network*: 3pp, Aug. 8, 2005.

American Red Cross., "Blood 101." 4pp., Dec. 11, 2007.

Anand et al., "Monitoring formation of high intensity focused ultrasound (HIFU) induced lesions using backscattered ultrasound." *Acoustical Society of America*; Mar. 10, 2004.

Anand et al., "Using the ATL 1000 to Collect Domodulated RF Data for Monitoring HIFU Lesion Formation." *Presented at SPIE Medical Imaging 2003*. 11pp, 2003.

Bachmann et al., "Targeting Mucosal Addressin Cellular Adhesion Molecule (MAdCAM)-1 to Noninvasively Image Experimental Crohn's Disease." *Gastroenterology*; vol. 130: 8-16, 2006.

Bauer et al., "Ultrasound Imaging with SonoVue: Low Mechanical Index Real-Time Imaging." *Acad. Radiol.*; vol. 9, Suppl. 2: S282-S284, 2002.
Beard et al., "An Annular Focus Ultrasonic Lens for Local Hyperthermia Treatment of Small Tumors." *Ultrasound in Medicine & Biology*; vol. 8, No. 2: 177-184, 1982.
Bokarewa et al., "Tissue factor as a proinflammatory agent." *Arthritis Research*, vol. 4: 190-195, Jan. 10, 2002.
Bots et al., "Intima Media Thickness as a Surrogate Marker for Generalised Atherosclerosis." *Cardiovascular Drugs and Therapy*, ProQuest Medical Library; vol. 16, No. 4: 341-351, Jul. 2002.
Brayman et al., "Erosion of Artificial Endothelia In Vitro by Pulsed Ultrasound: Acoustic Pressure, Frequency, Membrane Orientation and Microbubble Contrast Agent Dependence." *Ultrasound in Medicine & Biology*; vol. 25, No. 8: 1305-1320, 1999.
Buller et al., "Accurate Three-dimensional Wall Thickness Measurement From Multi-Slice Short-Axis MR Imaging." *Computers in Cardiology*, 245-248, 1995.
Campbell et al. "Pulsatile Echo-encephalography." *Acta Neurologica Scandinavica Supplementum 45*, vol. 46: 1-57, 1970.
Chao et al., "Aspheric lens design." *Ultrasonics Symposium, 2000 IEEE*, vol. 2: Abstract Only, Oct. 2000.
Chen et al., "A comparison of the fragmentation thresholds and inertial cavitation doses of different ultrasound contrast agents." *Journal of the Acoustical Society of America*, vol. 113, No. 1: 643-665, Jan. 2003.
Chen et al., "Inertial Cavitation Dose and Hemolysis Produced In Vitro With or Without Optison." *Ultrasound in Medicine & Biology*, vol. 29, No. 5: 725-737, 2003.
Chong et al., "Tissue Factor and Thrombin Mediate Myocardial Ischemia-Reperfusion Injury." *The Society of Thoracic Surgeons*, vol. 75: S649-655, 2003.
Dahl et al., "Simultaneous Assessment of Vasoreactivity Using Transcranial Doppler Ultrasound and Cerebral Blood Flow in Healthy Subjects." *Journal of Cerebral Blood Flow and Metabolism*, vol. 14, No. 6: 974-981, 1994.
Dayton et al., "The magnitude of radiation force on ultrasound contrast agents." *Journal of the Acoustical Society of America*, vol. 112, No. 5, Part 1: 2183-2192, Nov. 2002.
Dempsey et al., "Thickness of Carotid Artery Atherosclerotic Plaque and Ischemic Risk." *Neurosurgery*, vol. 27, No. 3: 343-348, 1990.
Ebbini et al., "Image-guided noninvasive surgery with ultrasound phased arrays." *SPIE*, vol. 3249: 230-239, Apr. 2, 1998.
Everbach et al., "Cavitational Mechanisms in Ultrasound-Accelerated Thrombolysis at 1 MHz." *Ultrasound in Medicine & Biology*, vol. 26, No. 7: 1153-1160, 2000.
Ewert et al., "Anti-myeloperoxidase antibodies stimulate neutrophils to damage human endothelial cells." *Kidney International*, vol. 41: 375-383, 1992.
Ganapathy et al., "A New General Triangulation Method for Planar Contours." *Computer Graphics* vol. 16, No. 3:69-75, 1982.
Gao et al., "Imaging of the Elastic Properties of Tissue—A Review." *Ultrasound in Medicine & Biology*, vol. 22, No. 8: 959-977, 1996.
Guzman et al., "Ultrasound—Mediated Disruption of Cell Membranes. I. Quantification of Molecular uptake and Cell Viability. / II. Heterogeneous effects on cells." *Journal of the Acoustical Society of America*, vol. 110, No. 1: 588-606, Jul. 2001.
Hadimioglu et al., "High-Efficiency Fresnel Acoustic Lenses." *Ultrasonics Symposium 1993 IEEE*: 579-582, 1993.
Hatangadi, Ram. "A Novel Dual Axis Multiplanar Transesophageal Ultrasound Probe for Three-Dimensional Echocardiograph."_*University of Washington, Department of Sciences and Engineering*, vol. 55-11B: Abstract 1pg, 1994.
Holt et al., "Bubbles and Hifu: the Good, the Bad and the Ugly." *Boston University, Department of Aerospace and Mechanical Engineering*: 120-131, 2002.
Hubka et al., "Three-dimensional echocardiographic measurement of left ventricular wall thickness: In vitro and in vivo validation." *Journal of the American Society of Echocardiography*, vol. 15, No. 2: 129-135, 2002.
Hwang et al., "Vascular Effects Induced by Combined 1-MHz Ultrasound and Microbubble Contrast Agent Treatments In Vivo." *Ultrasound in Medicine & Biology*, vol. 31, No. 4: 553-564, 2005.
Hynynen et al., "Potential Adverse Effects of High-Intensity Focused Ultrasound Exposure on Blood Vessels In Vivo." *Ultrasound in Medicine & Biology*, vol. 22, No. 2: 193-201, 1996.
Iannuzzi et al., "Ultrasonographic Correlates of Carotid Atherosclerosis in Transient Ischemic Attack and Stroke." *Stroke*, ProQuest Medical Library, vol. 26, No. 4: 614-619, 1995.
Idell et al., "Fibrin Turnover in Lung Inflammation and Neoplasia." *American Journal of Respiratory and Critical Care Medicine*, vol. 163: 578-584, 2001.
Indman, Paul. "Alternatives in Gynecology." *Hysteroscopy*, OBGYN.net, 2000. http://www.gynalternatives.com/hsc.html.
Kaczkowski et al., "Development of a High Intensity Focused Ultrasound System for Image-Guided Ultrasonic Surgery." *Ultrasound for Surgery*, 2001. <http://cimu.apl.washington.edu/hifusurgerysystem.html>.
Kang et al., "Analysis of the Measurement Precision of Arterial Lumen and Wall Areas Using High-Resolution MRI." *Magnetic Resonance in Medicine*, vol. 44: 968-972, 2000.
Klibanov et al., "Detection of Individual Microbubbles of an Ultrasound contrast Agent: Fundamental and Pulse Inversion Imaging." *Academy of Radiology*, vol. 9, Suppl. 2: S279-S281, 2002.
Klingelhöfer et al., "Chapter 4: Functional Ultrasonographic Imaging" In Babikian VL, Wechsler LR, eds. *Transcranial Doppler Ultrasonography*. Woburn, MA: Butterworth-Heinemann, 49-66, 1999.
Kudo et al., "Study on Mechanism of Cell Damage Caused by Microbubbles Exposed to Ultrasound." *Ultrasound in Medicine & Biology*, vol. 29, Supplement: 4pp, 2003.
Lalonde et al., "Field conjugate acoustic lenses for ultrasound hyperthermia." *Ultrasonics, Ferroelectrics and Frequency Control, IEEE Transactions*, vol. 40, Issue 5: Abstract 1pg., Sep. 1993.
Markwalder et al., "Dependency of Blood Flow Velocity in the Middle Cerebral Artery on End-Tidal Carbon Dioxide Partial Pressure—A Transcranial Ultrasound Doppler Study." *Journal of Cerebral Blood Flow and Metabolism*, vol. 4, No. 3: 368-372, 1984.
Miller et al., "A Review of In Vitro Bioeffects of Inertial Ultrasonic Cavitation From a Mechanistic Perspective." *Ultrasound in Medicine & Biology*, vol. 22, No. 9: 1131-1154, 1996.
Miller et al., "Diagnostic ultrasound activation of contrast agent gas bodies induces capillary rupture in mice." *PNAS*, vol. 97, No. 18: 10179-10184, 2000.
Ng et al., "Therapeutic Ultrasound: Its Application in Drug Delivery." *Medicinal Research Reviews*, vol. 22, No. 2: 204-233, 2002.
O'Leary et al., "Carotid-artery Intima and Media Thickness as a Risk Factor for Myocardial Infarction and Stroke in Older Adults." Cardiovascular Health Study Collaborative Research Group. *New England Journal of Medicine*, vol. 340, No. 1: 14-22, Jan. 7, 1999.
Ostensen et al., "Characterization and Use of Ultrasound Contrast Agents." *Academy of Radiology*, vol. 9, Suppl. 2: S276-S278, 2002.
Owaki et al., "The Ultrasonic Coagulating and Cutting System Injuries Nerve Function." *Endoscopy*, vol. 34, No. 7: 575-579, 2002.
Pignoli et al., "Intimal plus medial thickness of the arterial wall: a direct measurement with ultrasound imaging." *Circulation*, vol. 74, No. 6:1399-1406, Dec. 1986.
Poliachik et al., "Activation, Aggregation and Adhesion of Platelets Exposed to High-Intensity Focused Ultrasound." *Ultrasound in Medicine & Biology*, vol. 27, No. 11: 1567-1576, 2001.
Poliachik et al., "Effect of High-Intensity Focused Ultrasound on Whole Blood With or Without Microbubble Contrast Agent." *Ultrasound in Medicine & Biology*, vol. 25, No. 6: 991-998, 1999.
Porter et al., "Ultrasound, Microbubbles and Thrombolysis." *Progress in Cardiovascular Diseases*, vol. 44, No. 2: 101-110, Oct. 2001.
Rivens et al., "Vascular Occlusion Using Focused Ultrasound Surgery for Use in Fetal Medicine." *European Journal of Ultrasound*, vol. 9: 89-97, 1999.
Rosen et al., "Vascular Occlusive Diseases." 37pp., revised 2002.
Rosenschein et al., "Shock-Wave Thrombus Ablation, A New Method for Noninvasive Mechanical Thrombolysis." *The American Journal of Cardiology*, vol. 70, Issue 15: Abstract, Nov. 15, 1992.
Rosenschein et al., "Ultrasound Imaging-Guided Nonivasive Ultrasound Thrombolysis-Preclinical Results." *Circulation*, vol. 102: 238-245, 2000. <http://www.circulationaha.com.org>.

Schulte-Altedorneburg et al., "Accuracy of in Vivo Carotid B-Mode Ultrasound Compared with Pathological Analysis: Intima-Media Thickening, Lumen Diameter, and Cross-Sectional Area." *Stroke*, vol. 32, No. 7: 1520-1524, 2001.
Tachibana et al., "Albumin Microbubble Echo-Contrast Material as an Enhancer for Ultrasound Accelerated Thrombolysis." *Circulation*, vol. 92: 1148-1150, 1995.
Tachibana et al., "The Use of Ultrasound for Drug Delivery." *Echocardiography*, vol. 18, No. 4: 323-328, May 2001.
Tardy et al., "In Vivo Ultrasound Imaging of Thrombi Using a Target-specific Contrast Agent." *Academy of Radiology*, vol. 9, Suppl. 2: S294-S296, 2002.
Vaezy et al., "Acoustic surgery." *Physics World*: 35-39, Aug. 2001.
Vaezy et al., "Hemostasis and Tumor Treatment using High Intensity Focused Ultrasound: Experimental Investigations and Device Development." *First International Workshop on the Application of HIFU in Medicine*: 46-49, 2001.
Vaezy et al., "Hemostasis using high intensity focused ultrasound." *European Journal of Ultrasound*, vol. 9: 79-87, 1999.
Vaezy et al., "Intra-operative acoustic hemostasis of liver: production of a homogenate for effective treatment." *Ultrasonics*, vol. 43: 265-269, 2005.
Von Land et al., "Development of an Improved Centerline Wall Motion Model." *IEEE*: 687-690, 1991.
Watkin et al., "Multi-Modal Contrast Agents: A First Step." *Academy of Radiology*, vol. 9, Suppl. 2: S285-S287, 2002.
Wickline et al., "Blood Contrast Enhancement with a Novel, Non-Gaseous Nanoparticle Contrast Agent." *Academy of Radiology*, vol. 9, Suppl. 2: S290-S293, 2002.
Williamson et al., "Color Doppler Ultrasound Imaging of the Eye and Orbit." *Survey of Ophthamology*, vol. 40, No. 4: 255-267, 1996.
Yu et al., "A microbubble agent improves the therapeutic efficiency of high intensity focused ultrasound: a rabbit kidney study." *Urological Research*, PubMed: Abstract, 2004.
N.a., "Cavitation." Ultrasound TIP—U.S. Database: Dec. 12, 2007.
N.a., "Mechanical Bioeffects in the Presence of Gas-Carrier Ultrasound Contrast Agents." *Journal of Ultrasound & Medicine*, vol. 19: 120-142, 2000.
N.a., "Breast Cancer—Insightec: focused ultrasound for non invasive treatment." FAQ, 2000. <http://www.exablate2000.com/physicians_faq.html>.

* cited by examiner

FIG. 2
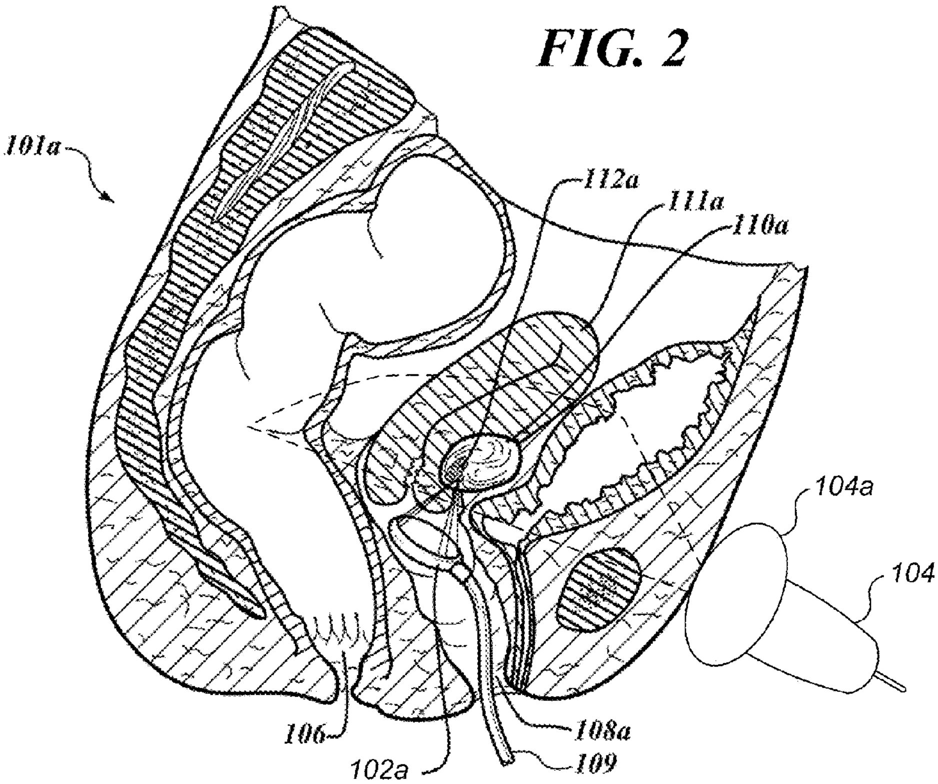
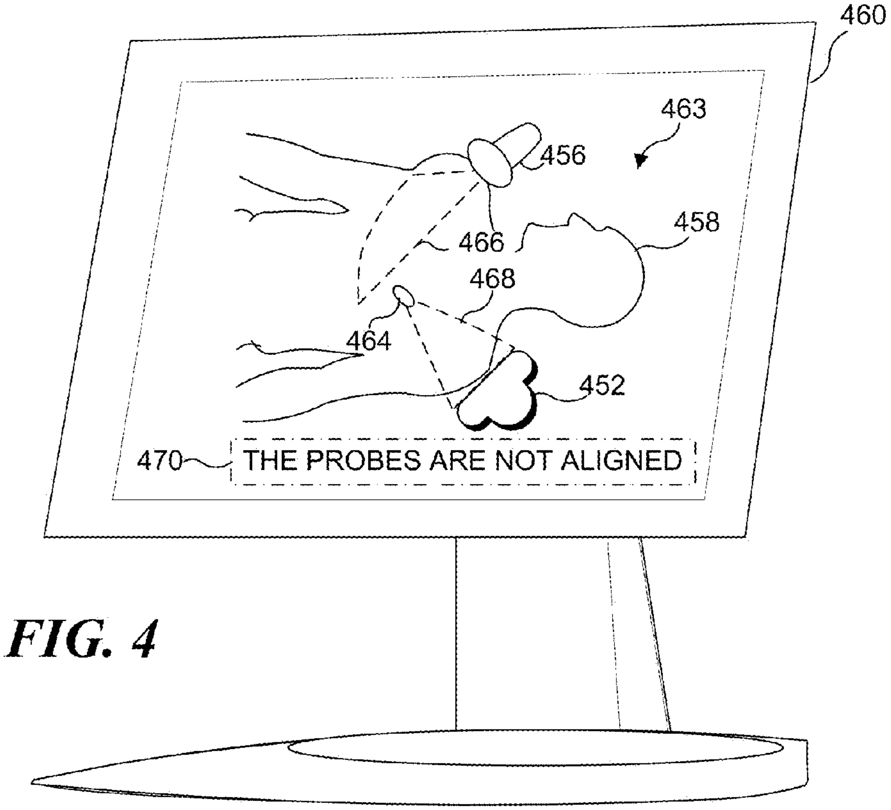
FIG. 4

METHODS FOR USING HIGH INTENSITY FOCUSED ULTRASOUND AND ASSOCIATED SYSTEMS AND DEVICES

RELATED APPLICATIONS

This application is a divisional of a patent application Ser. No. 11/928,667, filed on Oct. 30, 2007, which itself is a divisional of a patent application Ser. No. 10/977,339, filed on Oct. 29, 2004, and now issued as U.S. Pat. No. 7,520,856, the benefit of the filing date of which is hereby claimed under 35 U.S.C. §120. Parent application Ser. No. 10/977,339 is based on a prior provisional application Ser. No. 60/516,099, filed on Oct. 31, 2003, the benefit of the filing date of which is hereby claimed under 35 U.S.C. §119(e). Further, parent application Ser. No. 10/977,339 is a continuation-in-part application of prior application Ser. No. 10/770,350, filed on Feb. 2, 2004, and now issued as U.S. Pat. No. 7,686,763, which itself is a continuation-in-part application of prior application Ser. No. 10/166,795, filed on Jun. 7, 2002 and now issued as U.S. Pat. No. 6,716,184, which itself is a divisional application of prior application Ser. No. 09/397,471, filed on Sep. 17, 1999 and now issued as U.S. Pat. No. 6,425,867, the benefit of the filing dates of which is hereby claimed under 35 U.S.C. §120.

GOVERNMENT RIGHTS

This invention was made with U.S. government support under Grant No. N00014-01-96-0630 and N00014-01-G-0460 awarded by the Department of the Navy and grant number 2 R42 HD38440-02 awarded by National Institutes of Health. The U.S. government has certain rights in this invention.

BACKGROUND

High intensity focused ultrasound (HIFU) has emerged as a precise, non-surgical, minimally-invasive treatment for benign and malignant tumors. At focal intensities (1000-10000 W/cm$^2$) that are 4-5 orders of magnitude greater than that of diagnostic ultrasound (approximately 0.1 W/cm$^2$), HIFU can induce lesions (i.e., localized tissue necrosis) at a small, well defined region deep within tissue, while leaving intervening tissue between the HIFU transducer and the focal point substantially unharmed. Tissue necrosis is a result of tissue at the focal point of the HIFU beam being heated to over 70° C. in a very short period of time (generally less than one second). Tissue necrosis also results from cavitation activity, which causes tissue and cellular disorganization. HIFU is currently being used clinically for the treatment of prostate cancer and benign prostatic hyperplasia, as well as the treatment of malignant bone tumors and soft tissue sarcomas. Clinical trials are currently being conducted for HIFU treatment of breast fibroadenomas, and various stage-4 primary and metastatic cancerous tumors of the kidney and liver.

Uterine fibroids are benign tumors of the uterus that cause abnormal uterine bleeding. The incidence of fibroids in women in their reproductive years has been estimated to be 20-25%, although autopsy studies show an incidence to be greater than 75%. Approximately ⅓ of women experiencing uterine fibroids will have a tumor that is symptomatic requiring treatment. Approximately 30% of all hysterectomies are related to the presence of uterine fibroids. Current treatment methods for uterine fibroids include both drug therapy and surgery. Experience with drug therapy shows almost a 100% rate of tumor reoccurrence once the drug therapy has stopped, and the drug therapy has numerous undesirable side effects. The rate of reoccurrence is significantly less for the surgical therapy (about 15%). Unfortunately, most current procedures for removing uterine fibroids are based on invasive surgical techniques, which require a significant recovery period and involve significant risks (such as blood loss, damage to related organs, and the ever present risk of infection). It is estimated that uterine fibroid procedures in the United States alone account for 1.2 to 3.6 billion dollars in annual medical costs.

It appears that HIFU, delivered using a transvaginal transducer, could provide a minimally-invasive treatment for uterine fibroids. On Oct. 22, 2004, the United States Food and Drug Administration (FDA) approved the ExAblate 2000™ System; a new medical device that uses magnetic resonance image (MRI) guided focused ultrasound to target and destroy uterine fibroids. While MRI guided HIFU therapy offers an alternative to more invasive surgical techniques, MRI equipment is very expensive, not nearly as available as ultrasound imaging devices, and not nearly as portable as ultrasound imaging devices. It would be desirable to provide a less costly alternative to MRI guided HIFU therapy. Such treatment is expected to compare favorably with the costs for the current drug related therapy for the treatment of uterine fibroids and its efficacy should compare favorably with the higher success rate of the current surgical procedures, but without the attendant risks. It would further be desirable to provide additional techniques and tools to enhance HIFU therapy.

SUMMARY

A first aspect of the concepts disclosed herein is directed to method and apparatus configured to spatially track and display the relative positions of a HIFU focal point and an imaging plane from an ultrasound imager, so that a clinician can ensure that the HIFU focus remains in the image plane during HIFU therapy, thereby facilitating image guided HIFU therapy.

Another aspect of the concepts disclosed herein is directed to a transvaginal probe that includes a HIFU transducer optimized for the treatment of uterine fibroids from within the vagina. In one embodiment, the transvaginal probe includes a piezoceramic crystal bonded to an aluminum lens, to achieve a HIFU transducer having a focal length of about 4 cm. In another embodiment, the transvaginal probe includes a generally spoon-shaped transducer, which comprises a plurality of individual emitter elements.

Still another aspect of the concepts disclosed herein is a method for evaluating a quality of a coupling between a liquid-filled volume encompassing a HIFU transducer and a tissue interface. HIFU transducers, or a portion of a probe containing a HIFU transducer, are often disposed inside a liquid-filled membrane. The fluid helps enhance the propagation of the HIFU beam by coupling the beam into the adjacent tissue. If any air bubbles are present between the liquid-filled membrane and the tissue interface, they will negatively affect the HIFU treatment by reducing the power of the HIFU transferred to the tissue. In a first embodiment, a hysterscopei is used to visually detect the presence of such bubbles. The hysterscope can be a separate instrument, or can be integrated into the HIFU probe. In a second embodiment, the HIFU transducer is first energized at a lower power setting. If any air bubbles are present in the tissue interface, a portion of the low power beam emitted from the HIFU transducer will be reflected. Such reflections are detected, and if the amount of reflected energy is greater than a threshold value, specific steps will be taken to dislodge the air bubbles.

In a third embodiment, an imaging probe is used to image the therapy probe/tissue interface. Any air bubbles that are present in this interface will show up as a bright spot in the ultrasound image. If such bright spots are identified, proper steps are taken to dislodge the air bubbles. Techniques for dislodging air bubbles include repositioning the therapy probe to dislodge the air bubbles, inflating or deflating the liquid-filled membrane to dislodge the air bubbles, and flushing the interface with an irrigation liquid to dislodge the air bubbles.

Apparatus for implementing the above identified method is also disclosed herein.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1A (prior art) schematically illustrates an ultrasonic image generated during the simultaneous use of ultrasound for imaging and for providing HIFU therapy in a conventional manner, wherein noise due to the HIFU beam obscures the entire image;

FIG. 1B schematically illustrates an ultrasonic image generated during the simultaneous use of ultrasound for imaging and therapy, wherein pulsing of the HIFU limits the resulting noise to a portion of the image;

FIG. 1C schematically illustrates an ultrasonic image generated during the simultaneous use of ultrasound for imaging and therapy, wherein synchronized pulsing of the HIFU is used to shift the noise caused by the HIFU beam away from a treatment site displayed in the image;

FIG. 2 is a schematic view of a vaginal therapy probe that includes a therapeutic HIFU transducer and a transabdominal imaging probe being used for the simultaneous imaging and treatment of a tumor in a female reproductive system;

Figure 3:
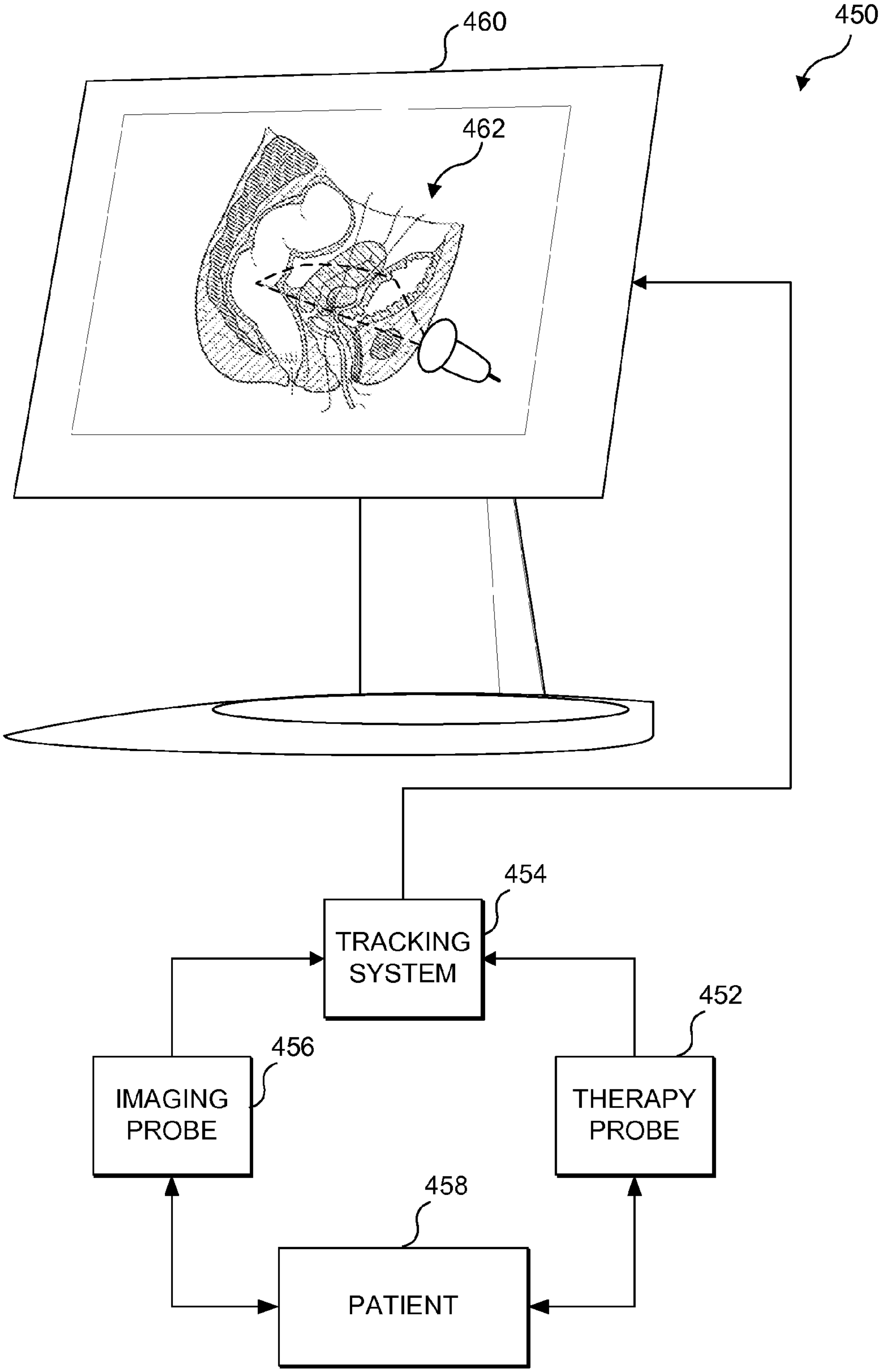
FIG. 3 is a block diagram schematically illustrating the elements of a system for use with the present invention to facilitate free hand visualization of the focal point of a HIFU beam during therapy.
Figure 5:
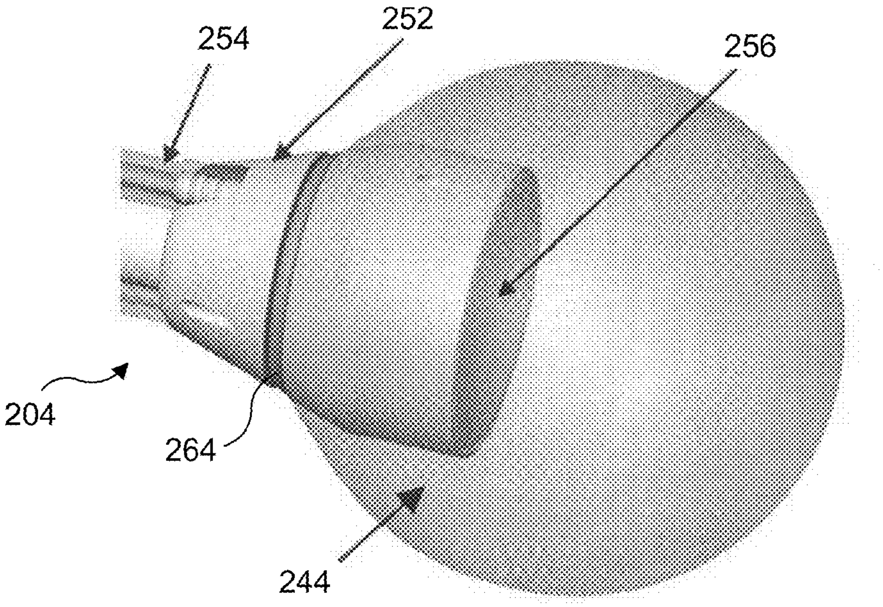
Figure 6:
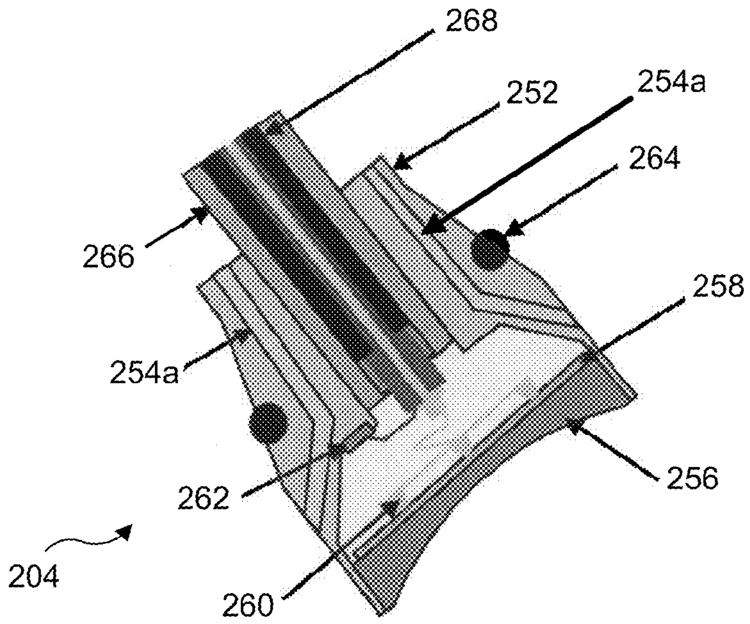
Figure 8A:
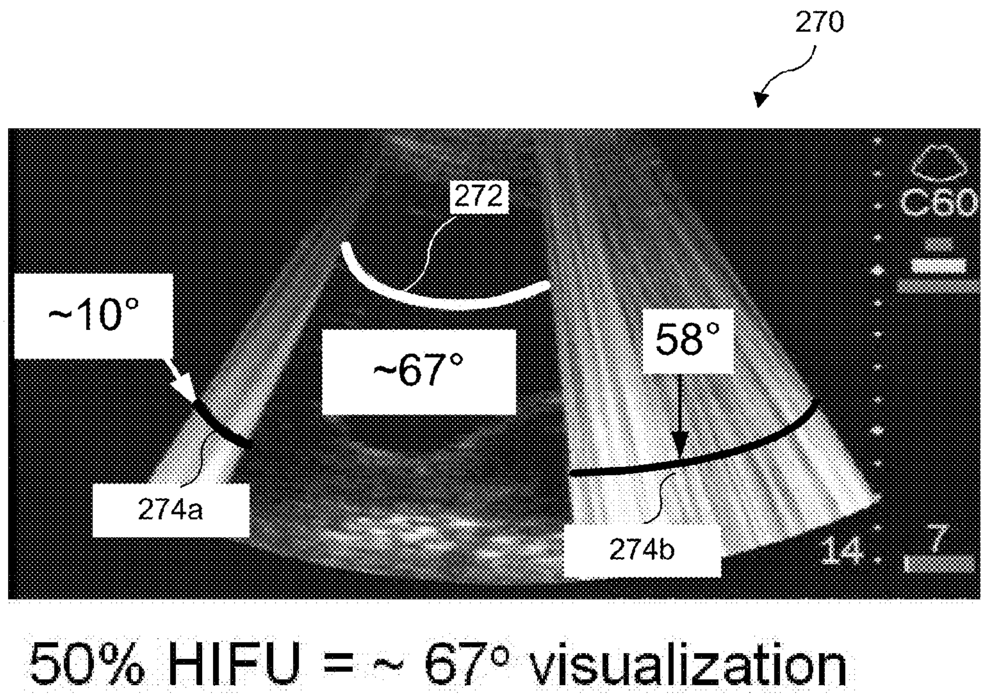
Figure 8B:
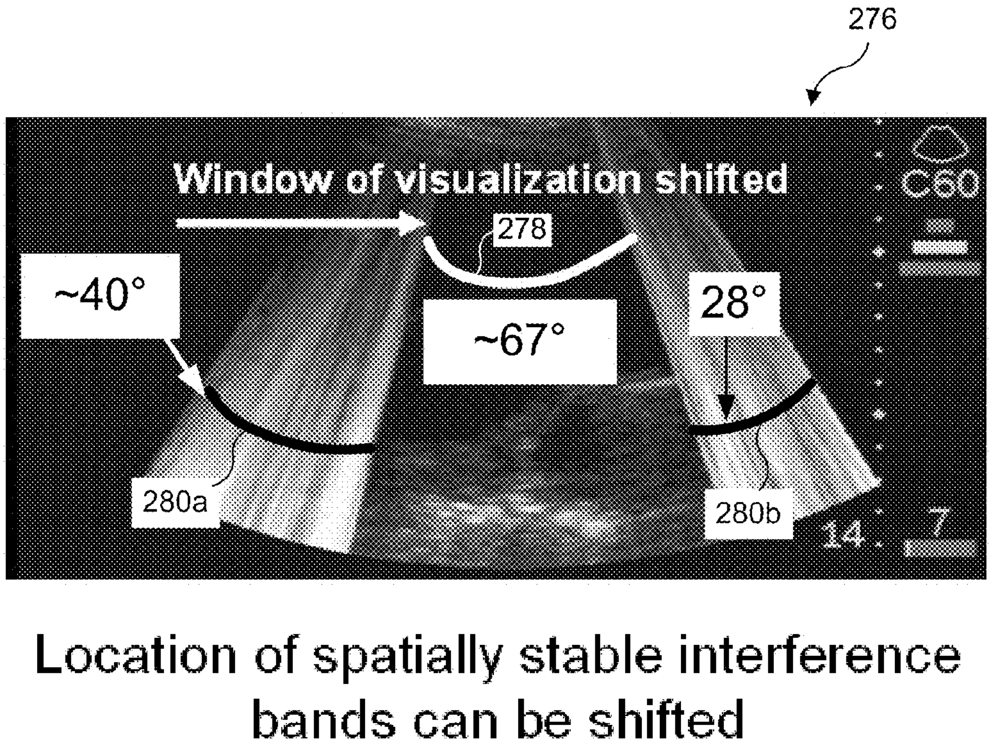
Figure 9:
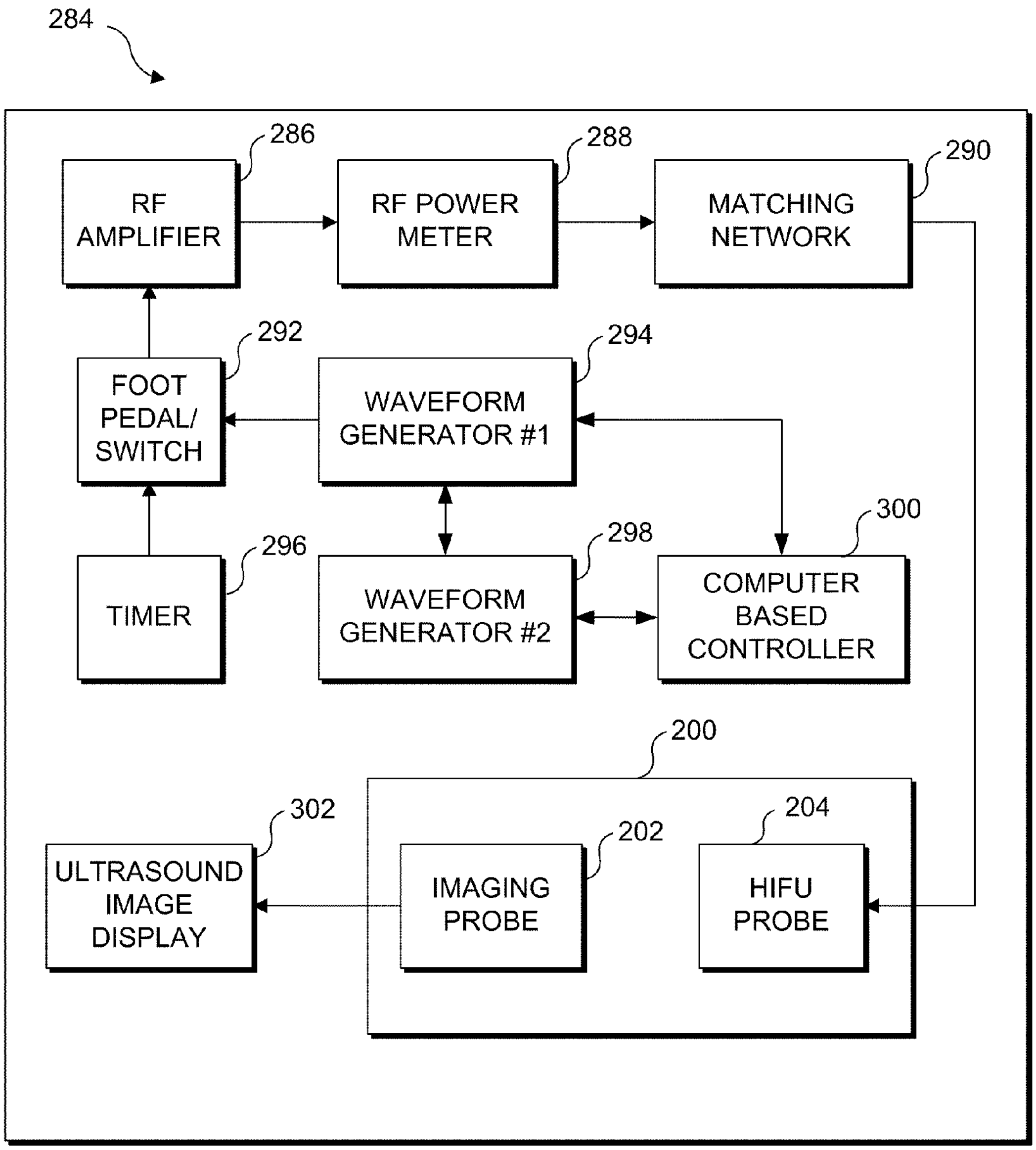
Figure 10A:
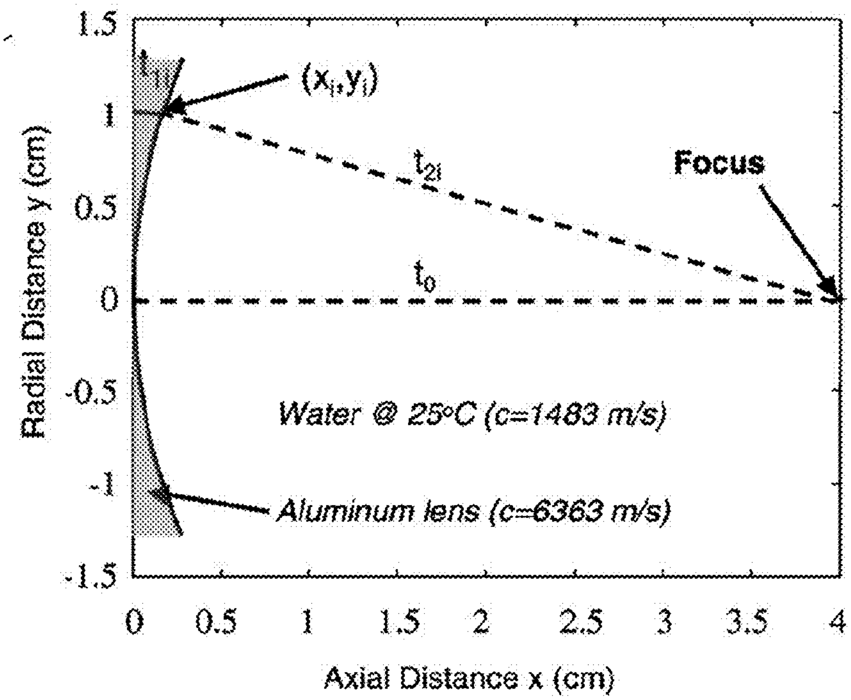
Figure 10B:
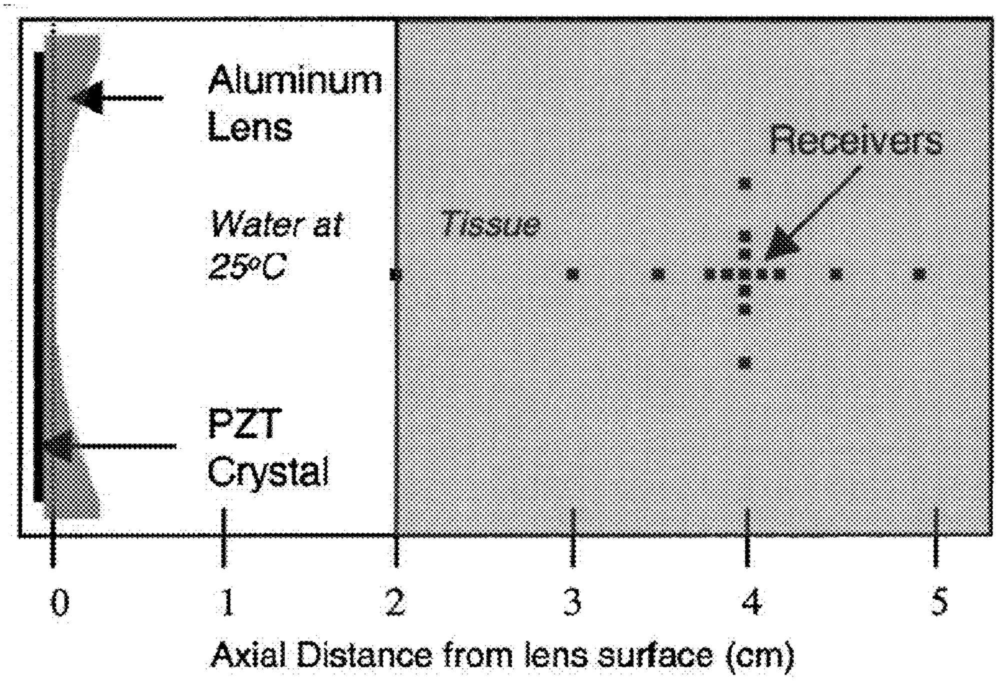
Figure 11A:
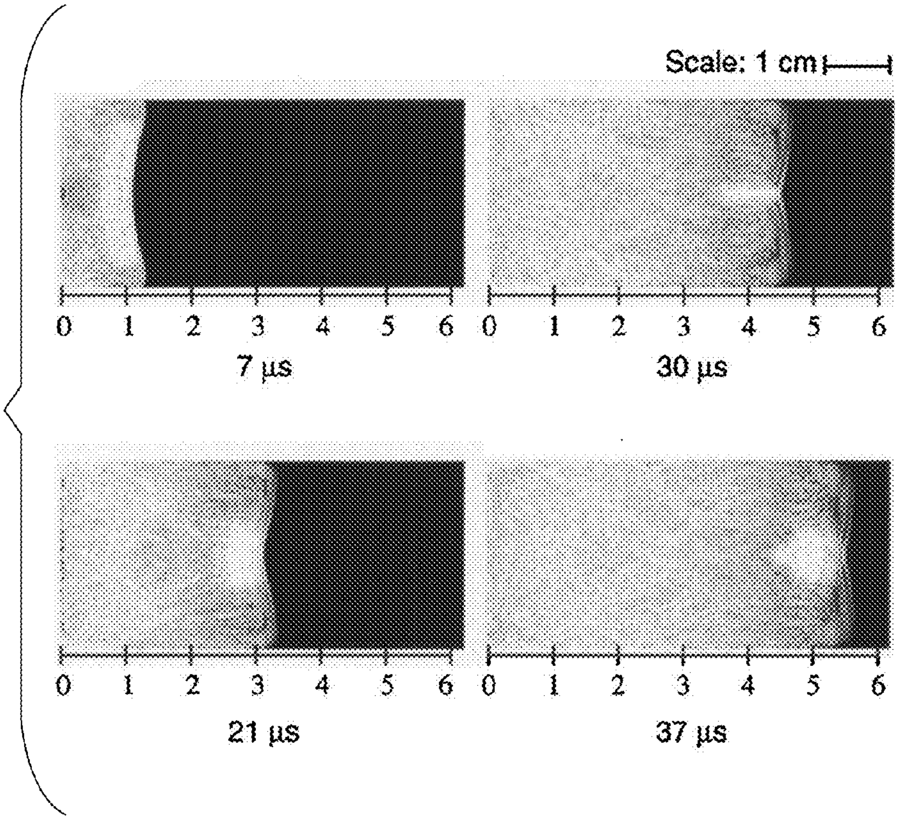
Figure 11B:
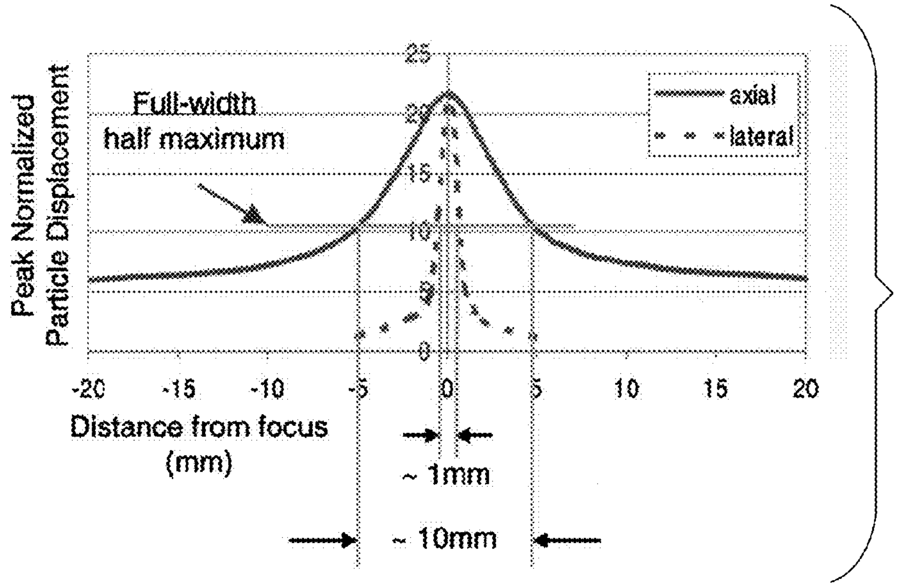
Figure 12A:
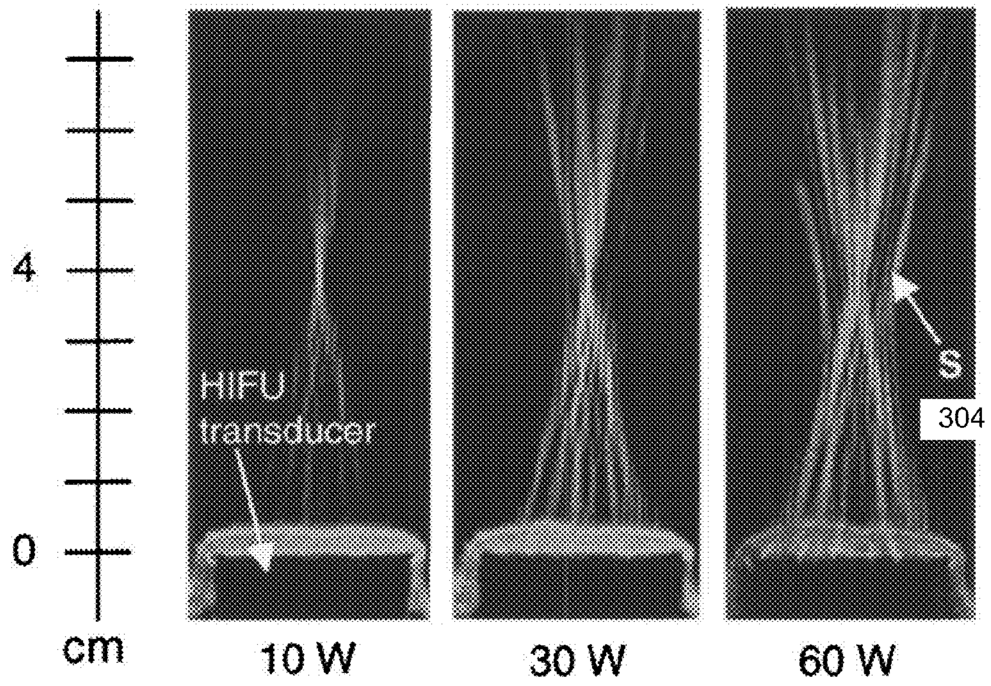
Figure 12B:
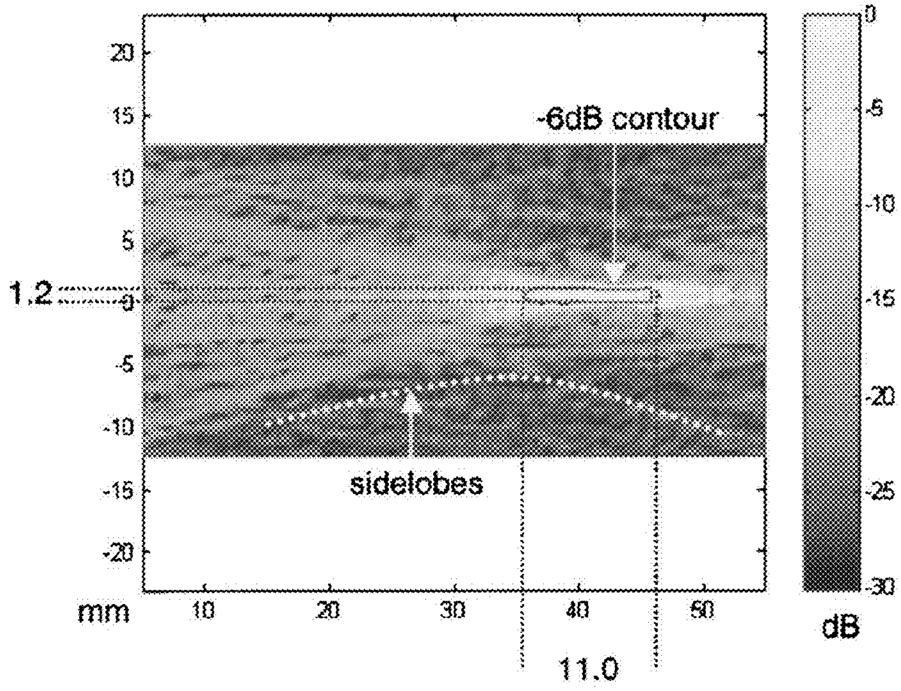
Figure 13:
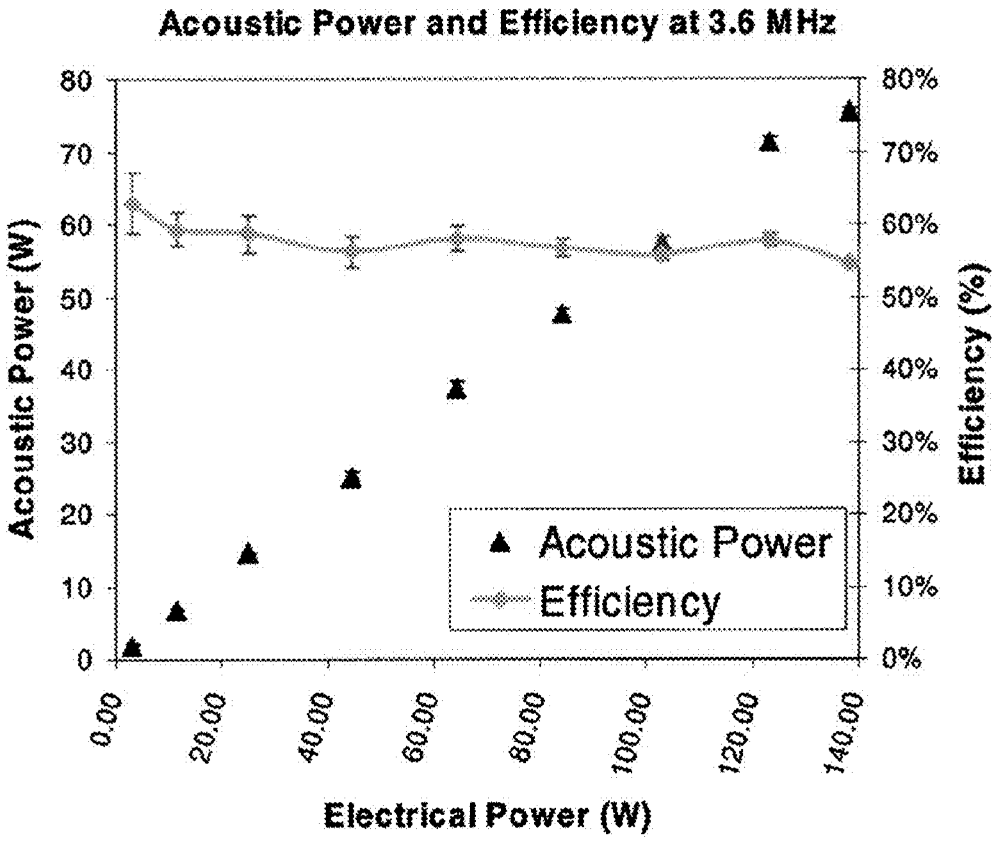
Figures 14A, 14B:
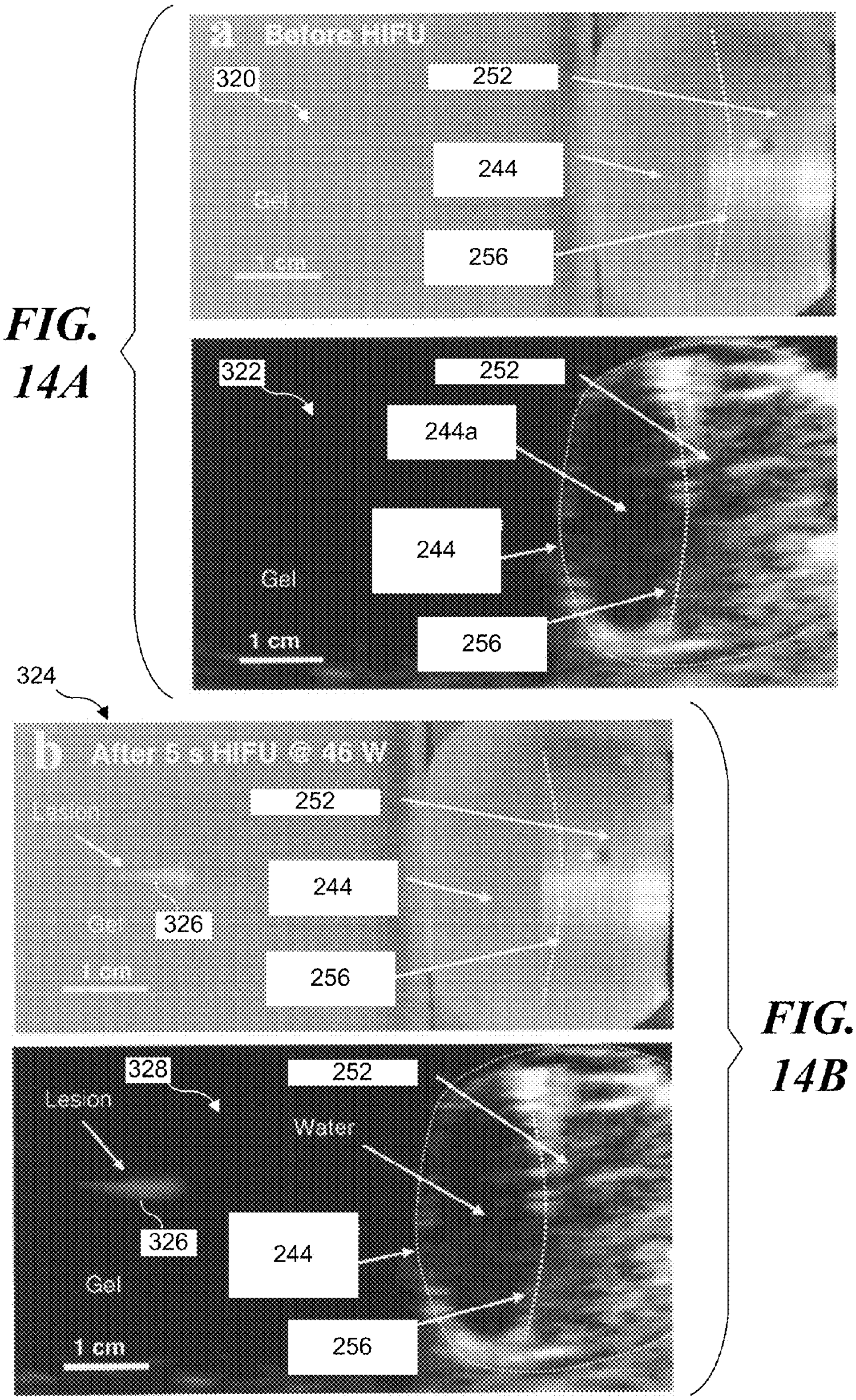
Figure 15A:
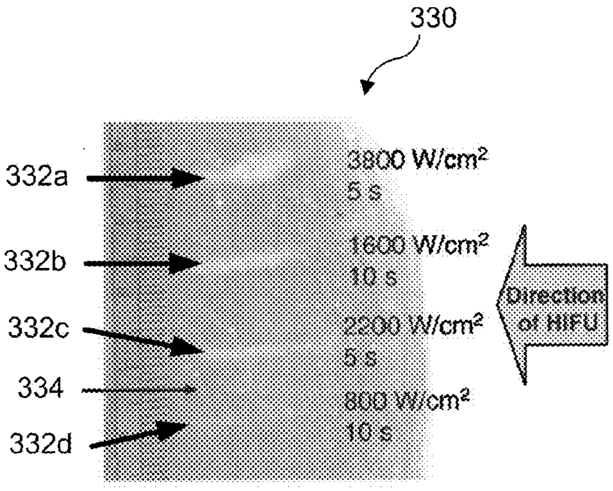
Figure 15B:
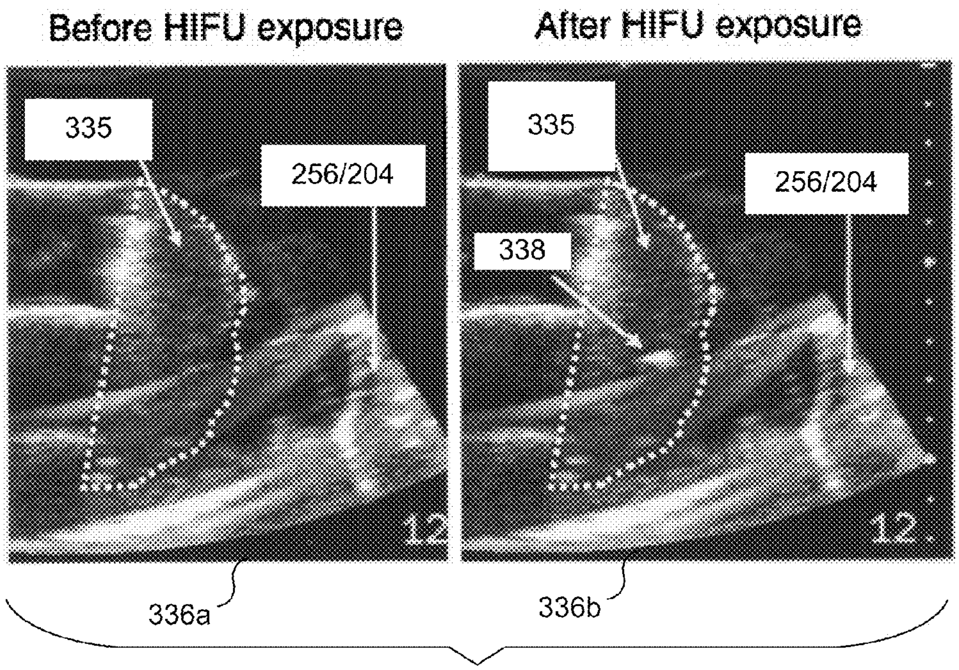
Figure 16:
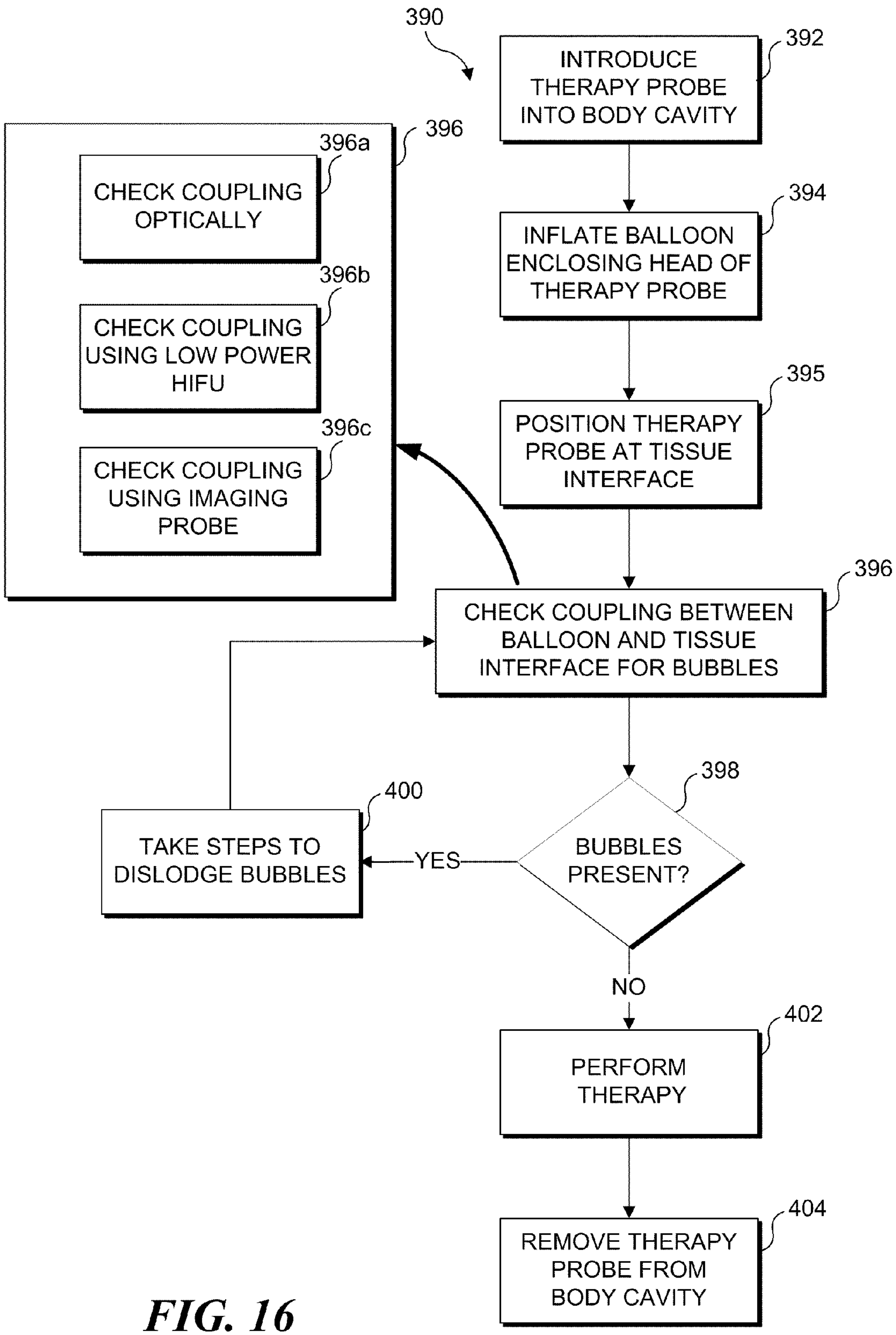
Figure 17A:
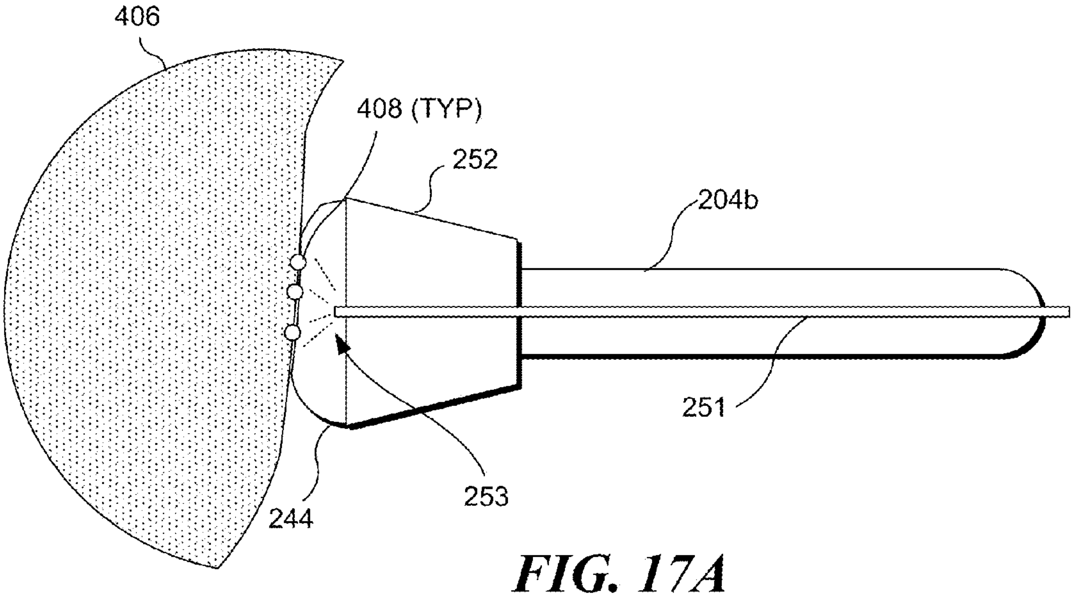
Figure 17B:
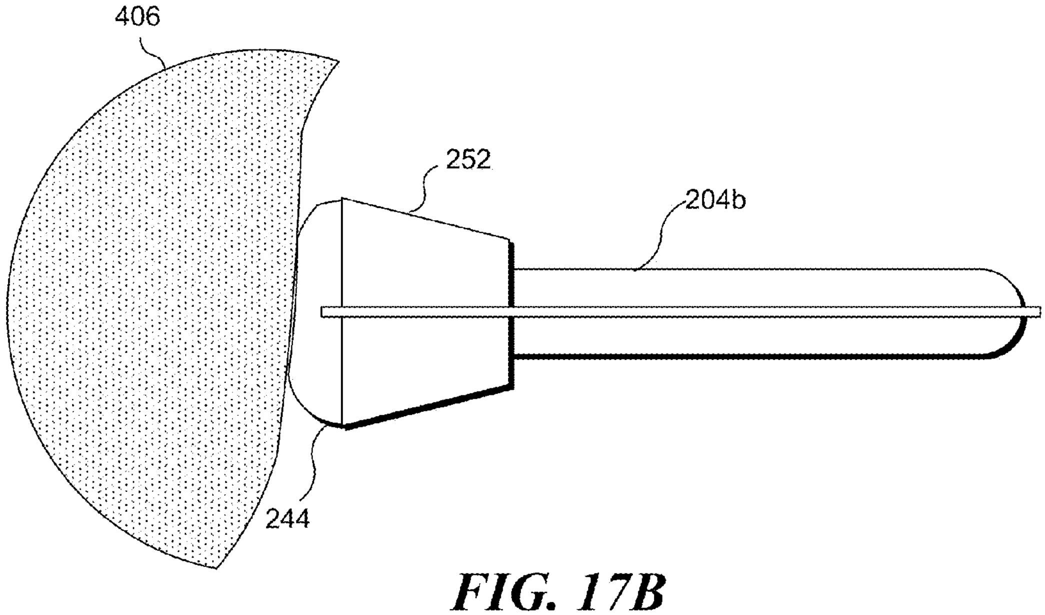
Figure 18:
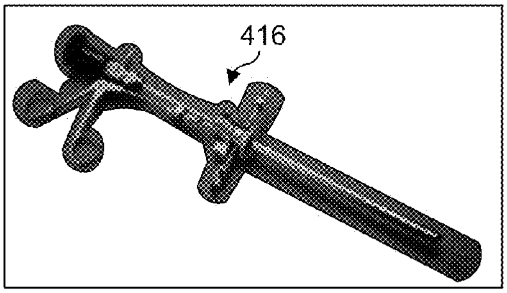
Figure 19A:
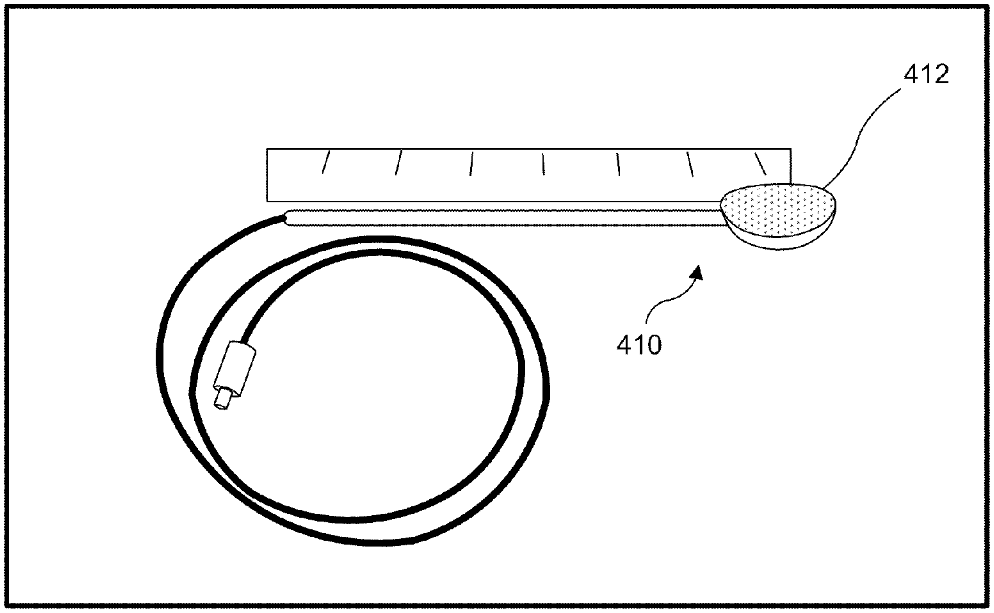
Figure 19B:
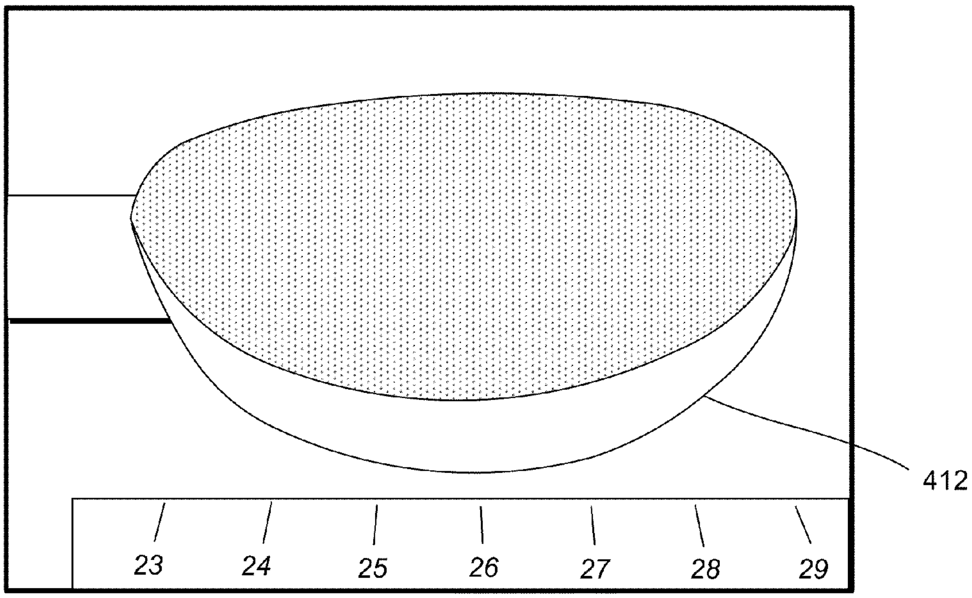
Figure 19C:
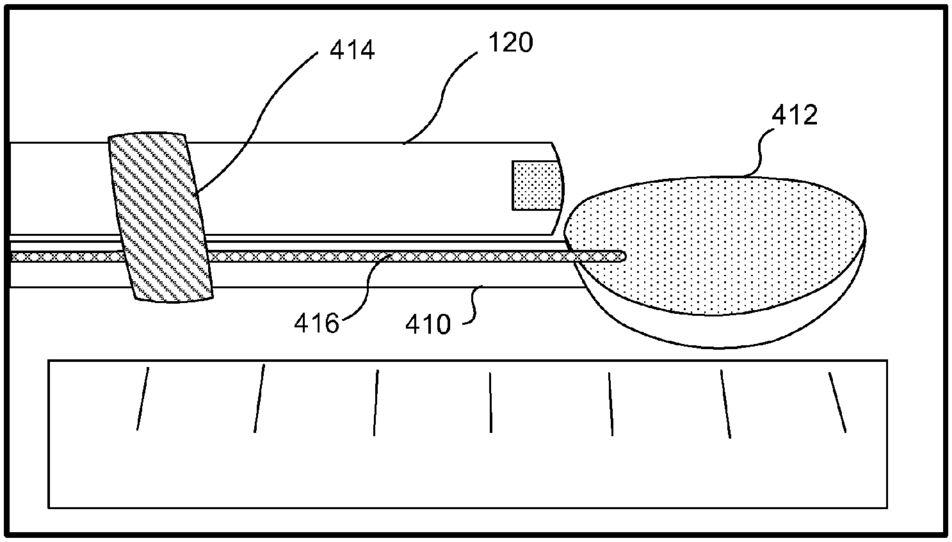
Figure 19D:
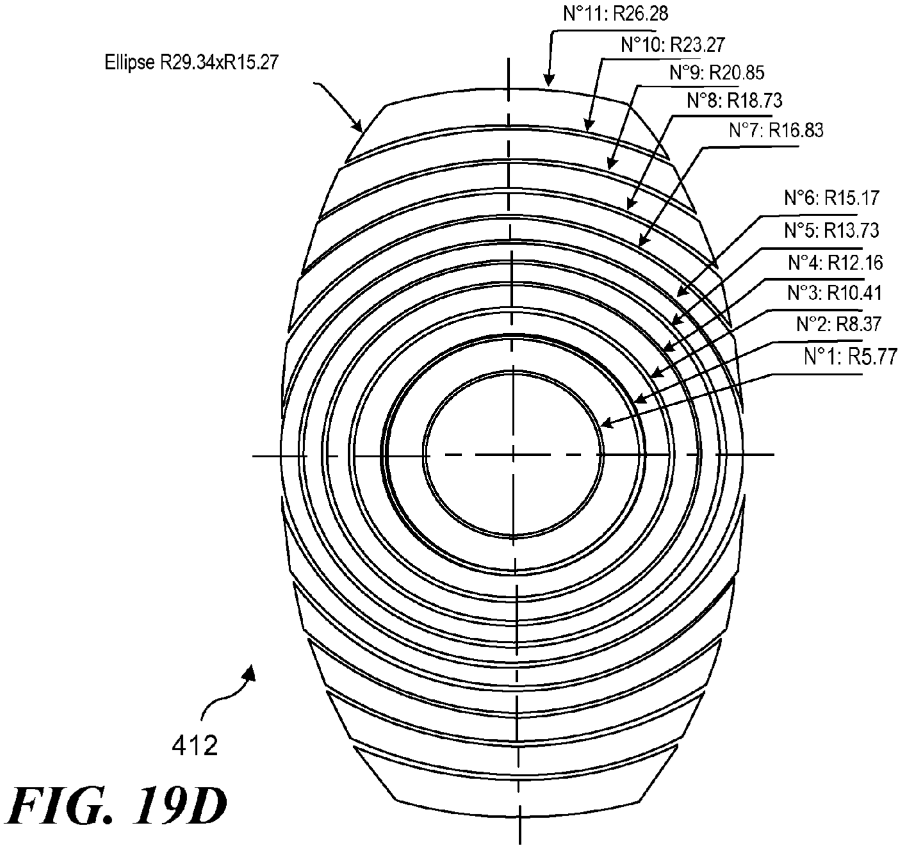

FIG. 4 schematically illustrates an exemplary image provided by the system of FIG. 3, enabling a clinician to determine how to manipulate a spatial relationship between an imaging probe and a therapy probe to ensure visualization of the focal point of a HIFU beam during therapy (noting that different treatment sites are being shown in the different Figures);

FIG. 5 schematically illustrates a distal end of an exemplary transvaginal HIFU therapy probe including an aluminum lens;

FIG. 6 schematically illustrates an internal view of part of the transvaginal HIFU therapy probe of FIG. 5;

FIGS. 7A-7F illustrate elements used to assemble a working embodiment of the transvaginal HIFU therapy probe of FIG. 5;

FIGS. 8A and 8B are ultrasound images illustrating how noise generated by the HIFU beam can be shifted to a portion of the ultrasound image that avoids interference with a visualization of the focal point of the HIFU beam during therapy;

FIG. 9 is a block diagram schematically illustrating the elements of a system for use with the present invention to facilitate visualization of the focal point of a HIFU beam during therapy;

FIGS. 10A and 10B graphically illustrate preferred geometries of the HIFU transducer and lens employed in the transvaginal HIFU therapy probe of FIG. 5;

FIG. 11A is a composite of images extracted from a computer simulation used to design the HIFU transducer for use in the transvaginal therapy probe of FIG. 5;

FIG. 11B graphically illustrates peak normalized particle displacements collected from the computer simulation used to design the HIFU transducer for use in the transvaginal therapy probe of FIG. 5, indicating estimated focal dimensions of 10 mm in length by 1 mm in width;

FIG. 12A is a composite of Schlieren images obtained during empirical testing of the HIFU transducer used in the transvaginal therapy probe of FIG. 5;

FIG. 12B graphically illustrates an acoustic field map created using data collected with a PVDF needle hydrophone during empirical testing of the HIFU transducer designed for use in the transvaginal therapy probe of FIG. 5, indicating focal point dimensions of 11 mm in length and 1.2 mm in width;

FIG. 13 graphically illustrates the correlation between electrical power and acoustic power for the HIFU transducer used in the transvaginal therapy probe of FIG. 5;

FIG. 14A is a composite image including both a photograph of the distal end of the transvaginal therapy probe of FIG. 5 coupled to a gel phantom and an ultrasound image of the distal end of transvaginal therapy probe of FIG. 5 coupled to the gel phantom;

FIG. 14B is a composite image including both a photograph and ultrasound image, substantially similar to those of FIG. 14A, after the application of HIFU therapy, wherein a lesion is visible in both the photograph and the ultrasound image;

FIG. 15A is a photograph of a turkey breast including a plurality of lesions formed using a HIFU beam generated with the transvaginal probe of FIG. 5;

FIG. 15B is a composite image including before and after ultrasound images showing the transvaginal probe of FIG. 5 being positioned to apply HIFU therapy to a turkey breast, wherein a lesion is visible in the after image;

FIG. 16 is a flowchart illustrating the logical steps implemented in a method for determining whether any air bubbles are present at an interface between a therapy probe and a mass of tissue, in accord with another aspect of the present invention;

FIG. 17A schematically illustrates a transvaginal therapy probe being coupled to a mass of tissue, so that a plurality of air bubbles are trapped at the tissue interface;

FIG. 17B schematically illustrates a transvaginal therapy probe being coupled to a mass of tissue, such that no air bubbles are trapped at the tissue interface;

FIG. 18 is a photograph of a prior art hysterscope that is useful to optically determine whether any air bubbles are present at the tissue interface;

FIG. 19A schematically illustrates a second embodiment of a transvaginal therapy probe in accord with the present invention;

FIG. 19B schematically illustrates a generally spoon shaped transducer of the transvaginal therapy probe shown in FIG. 19A;

FIG. 19C schematically illustrates the transvaginal therapy probe of FIG. 19A removably coupled to a prior art imaging probe and hysterscope, indicating how each instrument is used during a therapeutic procedure; and FIG. 19D schematically illustrates a plurality of emitter elements comprising the HIFU transducer in the transvaginal therapy probe of FIGS. 19A-C.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

The terms "therapeutic transducer," "HIFU transducer," and "high intensity transducer," as used herein and in the claims that follow all refer to a transducer that is capable of being energized to produce ultrasonic waves that are much more energetic than the ultrasonic pulses produced by an imaging transducer, and which can be focused or directed onto a discrete location, such as a treatment site in a target area. However, in at least one embodiment of the present invention, not all ultrasonic waves produced by such a transducer are necessarily at a high intensity, as is explained below.

When administering HIFU therapy, it is very desirable to be able to observe a treatment site, to ensure that lesions induced by the HIFU therapy are being produced at the desired location. Failure to properly aim the HIFU beam will result in undesired tissue necrosis of non target tissue. From a practical standpoint, this goal has not proven easy to accomplish when ultrasound is used to visualize the focal point, because the HIFU beam used for therapy completely saturates the signal provided by the imaging transducer. One analogy that might help to make this problem clear relates to the relative intensities of light. Consider the light coming from a star in the evening sky to be equivalent to the low power imaging ultrasound waves that are reflected from a target area toward the imaging transducer, while the light from the sun is equivalent to the HIFU generated by the therapy transducer. When the sun is out, the light from the stars is completely overwhelmed by the light from the sun, and a person looking into the sky is unable to see any stars, because the bright light from the sun makes the dim light coming from the stars substantially imperceptible. Similarly, the HIFU emitted by the therapy transducer completely overwhelms the ultrasonic waves produced by the imaging transducer, and any ultrasonic image generated is completely saturated with noise caused by the HIFU emitted from the therapeutic transducer.

Figure 1A:
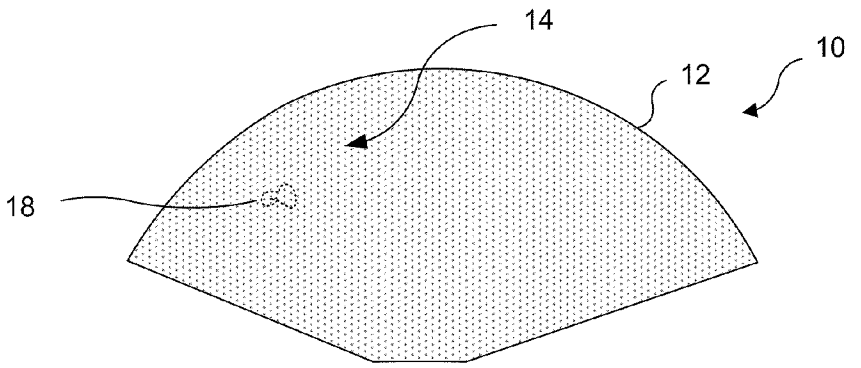

FIG. 1A illustrates an ultrasound image 10 in which a scanned image field 12 is completely obscured by noise 14, as is typical during the simultaneous reception of energy from a reflected imaging pulse and a HIFU wave (neither shown). In regard to ultrasound image 10, a clinician may desire to focus the HIFU wave on a treatment site 18. However, because noise 14 completely saturates scanned image field 12, it is virtually impossible to accurately focus the HIFU wave onto treatment site 18. If the therapy transducer is completely de-energized, noise 14 is eliminated from the scanned image field. However, under these conditions, the focal point of the HIFU wave will not be seen, and thus, the HIFU wave cannot be accurately focused on treatment site 18. While some change in echogenicity at the HIFU focal point will persist for a time after the HIFU wave is no longer present, any change in a position of the therapy transducer (or treatment site 18) will not register until the therapeutic transducer is re-energized, and thus, the HIFU wave cannot be focused in real time.

Some prior art systems have included a targeting icon in an ultrasound image to indicate the position of the known focal point of a specific HIFU transducer in a scanned image. While this icon may be helpful in determining whether the HIFU was previously focused, it still does not enable a clinician to observe real-time results. Once the HIFU therapeutic transducer is energized, the scanned ultrasound image is completely saturated with noise, and the clinician cannot monitor the progress of the treatment without again de-energizing the HIFU therapeutic transducer.

Figure 1B:
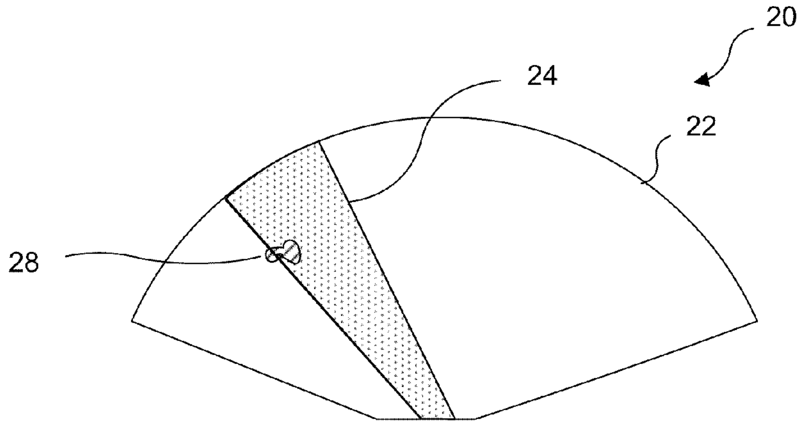

FIG. 1B illustrates one technique in which the effect of noise disrupting the ultrasound image is reduced. In FIG. 1B, the HIFU wave generated by the therapeutic transducer has been pulsed. This technique produces an ultrasound image 20, in which the location of noise 24 in a scanned field 22 is a function of the interference between the pulsed HIFU wave generated by the therapy transducer and the ultrasonic imaging ultrasound pulses generated by the scanning transducer. In FIG. 1B, noise 24 substantially masks a treatment site 28. This result will not occur in all cases, because to an observer, noise 24 will move across scanned filed 22 as the interference between the HIFU waves and the imaging pulses varies in time. Pulsing of the HIFU wave alone can thus enable the clinician to view a noise-free image of the treatment site only when noise 24 is randomly shifted to a different part of scanned field 22, away from the treatment site. However, this pulsing of the HIFU beam generates an image that is extremely distracting to a clinician, as noise 24 flickers across scanned field 22, making it difficult to concentrate and difficult to consistently determine where the focal point of the HIFU wave is relative to the treatment site, in real time.

Figure 1C:
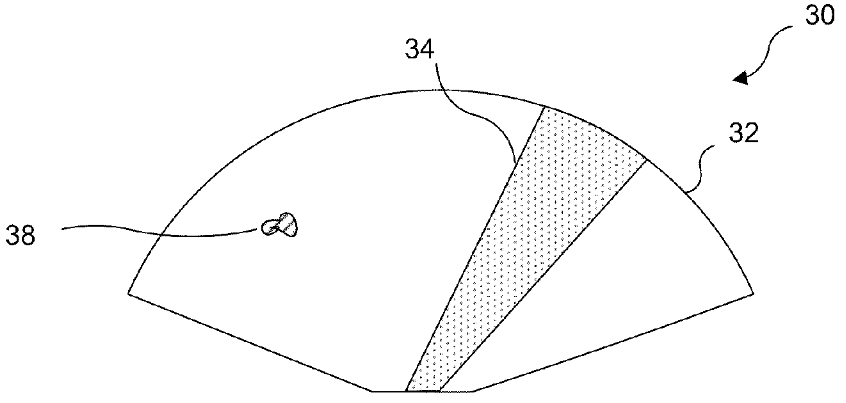

FIG. 1C illustrates an ultrasound image 30 in which a HIFU wave from a therapy transducer has been both pulsed and synchronized with respect to the ultrasonic imaging pulses from an imaging transducer, to ensure that noise 34 does not obscure a treatment site 38. In ultrasound image 30, noise 34 has been shifted to a location within a scanned field 32 of the image that is spaced apart from treatment site 38, by selectively adjusting both the pulsing and the synchronization of the HIFU wave relative to the image pulses. Preferably, noise 34 is shifted completely away from treatment site 38, enabling the clinician to view a noise-free, stable image of treatment site 38 that clearly shows the location of the focal point of the HIFU wave relative to the treatment site. Thus, the HIFU wave can be focused in real time onto treatment site 38, and a clinician can, in real time, view the therapeutic effects of the HIFU wave on treatment site 38. It will therefore be apparent that a clinician can de-energize the therapeutic transducer, terminating the generation of the HIFU wave as soon as a desired therapeutic effect has been achieved at the treatment site. In this manner, undesired effects on non target tissue can be minimized.

While combination imaging and therapy probes can be employed to achieve image guided HIFU therapy, many medical offices have access to transabdominal imaging probes. Thus, one aspect of the concepts disclosed herein is directed to using the relatively ubiquitous transabdominal ultrasound imaging probes with a transvaginal HIFU probe to achieve simultaneous imaging and administration of HIFU therapy for a treatment site. In FIG. 2, a HIFU transducer 102*a* is included on a vaginal probe 109, and an imaging transducer 104*a* is part of a transabdominal probe 104. Vaginal probe 109 has been inserted into a vaginal canal 108*a* and positioned to enable imaging transducer 104*a* of transabdominal probe 104 to be used in generating an ultrasonic image of a tumor 110*a*. Once tumor 110*a* has been located, HIFU transducer 102*a* is focused on a selected portion of tumor 110*a* to which the clinician desires to administer the HIFU therapy to generate a lesion 112*a*. The HIFU therapy is used to destroy the tumor by causing lesions of the blood vessels supplying oxygen and nutrients to the tumor, thereby generating a plurality of lesions similar to lesion 112*a*, so that the tumor withers away, or by destroying spaced-apart portions of the tumor. Particularly if the latter technique is used, the HIFU therapy will likely be repeated at intervals of several weeks. The time between successive therapy sessions enables macrophages in the patient's body to clear away or debride the necrotic tissue from the tumor so that it is reduced in size with each therapy session and is eventually destroyed.

It must be recognized that because HIFU transducer 102*a* and imaging transducer 104*a* are not both disposed on vaginal probe 109, maintaining the required spatial orientation between HIFU transducer 102*a* and imaging transducer 104*a*, such that the focal point of the HIFU beam provided by HIFU transducer 102*a* lies within the imaging plane provided by imaging transducer 104*a*, can be problematic. Once transabdominal probe 104 and vaginal probe 109 are properly positioned, if either probe (or the patient) changes position, the spatial orientation or relationship between the therapy and imaging probes may be changed, such that the focal point of the HIFU beam may no longer lie within the imaging plane provided by the imaging transducer. Clearly, such movement can undesirably result in the inability to monitor the effects of the HIFU therapy being administered, in real time.

Thus one aspect of the concepts disclosed herein is a system and method that enables free hand registration of the imaging and therapy probes. FIG. 3 schematically illustrates a system 450 that facilitates such free hand registration. System 450 includes a HIFU therapy probe 452, an ultrasound imaging probe 456, a tracking system 454, and a display 460. It should be understood that any type of HIFU therapy probe (configured for internal or external use), and any type of ultrasound imaging probe (configured for internal or external use), can be used in conjunction with system 450. Instead of using a physical or mechanical frame to maintain a spatial relationship between the HIFU therapy probe and the ultrasound imaging probe, system 450 relies on tracking system 454 to ensure that the spatial relationship between the HIFU therapy probe and the ultrasound imaging probe enables the focal point of the HIFU therapy probe to be visualized in the imaging plane generated by the ultrasound imaging probe. Tracking system 454 includes a processor that is able to keep track of the spatial relationship between the ultrasound imaging probe and the HIFU therapy probe. Such tracking systems are commercially available, and can be obtained from companies such as Ascension Technology, of Milton, Vt. Tracking systems for medical instruments are available based on several different technologies, including acoustic, light and magnetic based tracking systems, any of which could be used to implement tracking system 454. Magnetic based tracking systems (Ascension PC BIRD) that could be used for medical instruments are available from Mind Flux of Roseville, Australia.

System 450 functions as follows. HIFU therapy probe 452 and ultrasound imaging probe 456 are positioned relative to patient 458. The clinician can view an image 462 on a display 460. Image 462 includes a representation of patient 458, and the relative locations of ultrasound imaging probe 456 and HIFU therapy probe 452. Preferably image 462 will include a visual representation of the imaging plane provided by ultrasound imaging probe 456, and the HIFU beam generated by HIFU therapy probe 452. The clinician can determine from image 462 whether or not ultrasound imaging probe 456 and HIFU therapy probe 452 are properly aligned, such that the focal point of the HIFU beam can be visualized in an image provided by the ultrasound imaging probe. If the probes are not properly aligned, image 462 will provide the clinician a reference for determining how to reposition one or more of ultrasound imaging probe 456 and HIFU therapy probe 452, so that the focal point of the HIFU beam can be visualized in the ultrasound image. Depending on the size of display 460, the ultrasound image provided by ultrasound imaging probe 456 can be displayed along with image 462, or a separate display can be provided to display the ultrasound image generated by ultrasound imaging probe 456.

FIG. 4 is an enlarged view of display 460, including an image 463 (note a different treatment site is shown in FIG. 4 as compared to FIG. 3). The relative positions of ultrasound imaging probe 456, patient 458, and HIFU therapy probe 452 are presented in image 463. An image plane 466 provided by ultrasound imaging probe 456, a HIFU beam 468 provided by HIFU therapy probe 452, and a focal point 464 can be visualized in image 463. An optional message 470 informs the clinician that the probes are not properly aligned, which is apparent because imaging plane 466 and beam 468 do not overlap, and further, focal point 464 does not lie within image plane 466. While monitoring display 460 and image 463, the clinician can change the relative positions of ultrasound imaging probe 456 and HIFU therapy probe 452, until focal point 464 lies within imaging plane 466.

It should be noted image 463 is a two dimensional image, and those of ordinary skill in the art will readily recognized that even if the HIFU beam and the imaging plane overlap in two dimensions, they may not overlap in three dimensions. When image 463 indicates that the imaging plane and the HIFU beam overlap, a clinician can view the ultrasound image provided by the ultrasound imaging probe, to determine whether or not the focal point of the HIFU beam can actually be visualized in the ultrasound image. If not, this provides an indication that the spatial relationship and orientation between the imaging plane and the HIFU beam are not properly aligned, and the clinician can further manipulate the relative positions of the imaging probe and the HIFU therapy probe, until the focal point of the HIFU beam both overlaps the imaging plane in image 463, and can be visualized in the ultrasound image provided by the ultrasound imaging probe. It should also be understood that tracking system 454 can provide additional images from different perspectives (or image 463 could be rotated by tracking system 454) to provide feedback to a clinician indicating which direction the ultrasound imaging probe and/or the therapy probe need to be manipulated, so that the HIFU beam can be visualized in the image provided by the ultrasound imaging probe.

System 450 offers several advantages, including ease-of-use, the ability to visualize complex treatment strategies, and the ability to visualize complex tumor and anatomy geometries.

Another aspect of the concepts disclosed herein relates to exemplary therapy probes, some of which are optimized for vaginal therapy. These exemplary probes include the use of an aluminum lens in one exemplary embodiment, and a spoon shaped transducer array in another embodiment.

FIGS. 5 and 6 provide details regarding the distal end of a transvaginal therapy probe 204, while FIGS. 7A-7F are photographs illustrating the fabrication of a working model of transvaginal therapy probe 204. Referring to FIG. 5, expandable member 244 is coupled to a housing 252 using o-ring 264. In a working embodiment, housing 252 was implemented using brass, and a groove was included in the housing to accommodate o-ring 264 (see also FIG. 7E). A fluid line 254 is used to selectively inflate and deflate expandable member 244 (see also FIGS. 7E and 7F). An aluminum lens 256 is attached to the distal end of housing 252. As discussed in detail below, one embodiment of the present invention includes an aluminum lens that is used to focus a HIFU beam in the vaginal environment.

Figure 7A:
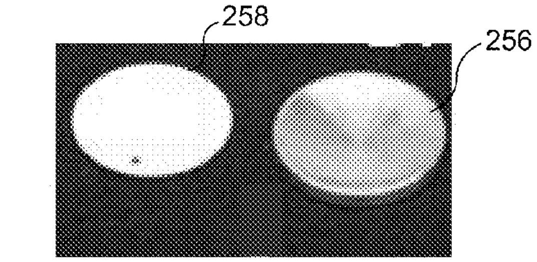
Figure 7B:
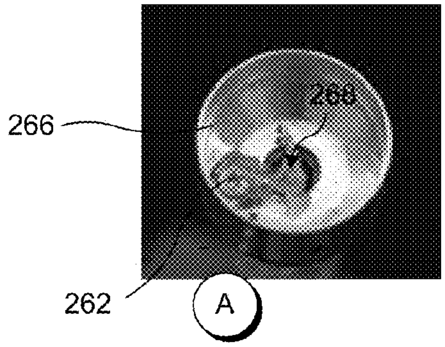
Figure 7C:
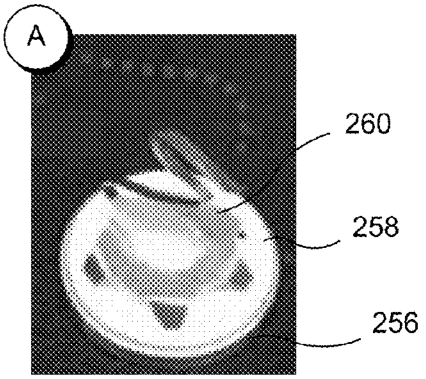
Figure 7D:
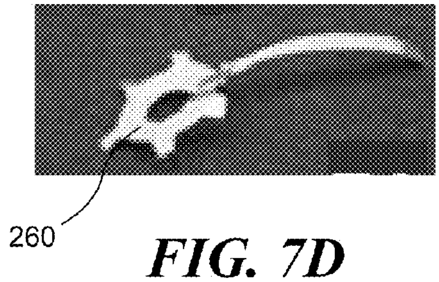

FIG. 6 illustrates a cross-sectional view of a distal end of transvaginal therapy probe 204. The HIFU transducer is implemented using a PZT-8 crystal 258, which is securely bonded to aluminum lens 256. FIG. 7A is a photograph of crystal 258 and aluminum lens 256 before they are bonded together. The crystal utilized in a working model is a flat, circular disk piezoceramic crystal (APC 880™, from American Piezoceramics, Duck Run, Pa.), with dimensions of about 25.4 mm in diameter and 0.59 mm in thickness (corresponding to half wavelength of APC 880 at 3.5 MHz). In the working prototype, the crystal was adhered to the aluminum lens with a thin layer (approximately 0.025 mm) of epoxy (Hysol RE2039™ and HD3561™, available from Loctite Corporation, Rocky Hill, Conn.). The bonding surfaces were roughened with a fiberglass brush and cleaned with acetone in an ultrasonic cleaner to ensure optimal bonding conditions. A custom built plastic (Delrin™) fixture and molds made of silicone rubber (RTV 630 A™ and RTV 630 ™ B, 10:1 by mass, available from GE Silicones, Waterford, N.Y.) ensured concentric alignment of the crystal and the lens during bonding. The crystal and lens were bonded under pressure (approximately 400 kPa), and the epoxy was allowed to set at a temperature of 150° C. for 3 hours.

Figure 7E:
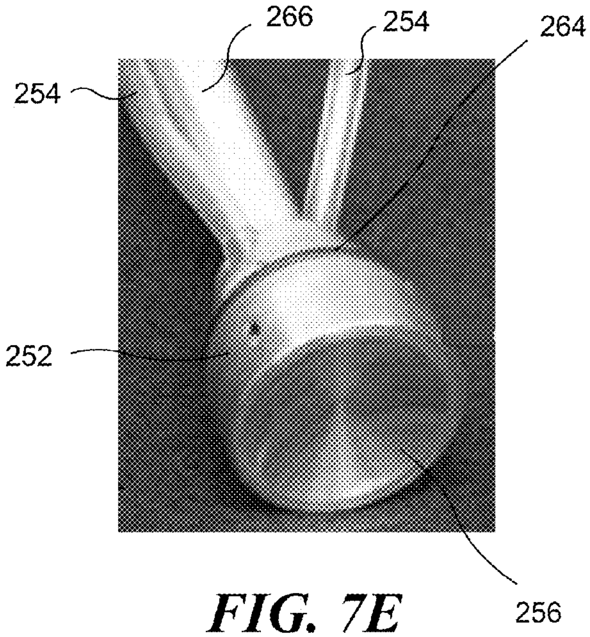
Figure 7F:
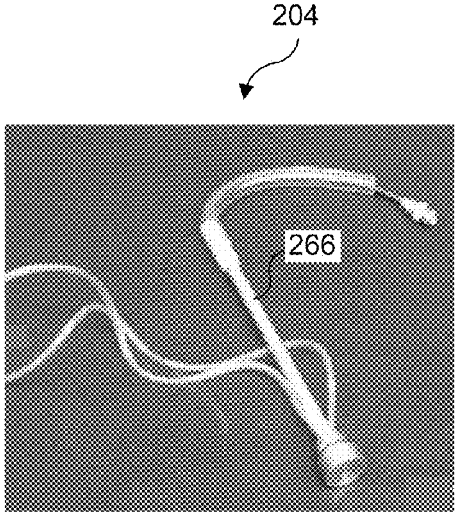

The main elongate body of the working model of transvaginal therapy probe 204 was implemented using a 9.52 mm (⅜") outer diameter hollow aluminum tube 266 (see also FIGS. 7E and 7F). Tube 266 was adhesively coupled (using Threadlocker 271™ adhesive, from Loctite Corporation, Rocky Hill, Conn.) to the brass housing (i.e., housing 252). A flexible coaxial cable 268 (RG-58 coaxial cable), approximately 10 cm longer than aluminum tube 266, was fed through the handle and its ground braiding was attached to the inside of the brass housing with a screw 262 for a ground connection (see FIG. 7B, in particular). To prevent electrical shorting, the inside of the brass housing, the braiding, and the screw were coated with epoxy, which provided isolation relative to the exposed coaxial cable center. The exposed coaxial cable at the end of the handle was encased in plastic tubing (R3603, ½" ID, from Saint-Gorbain Performance Plastics, Wayne, N.J.), and the tubing was secured to the handle using a plastic tubing connector to protect the transducer from water exposure. A conductive O-ring 260 (FIG. 7D) was cut from 0.25 mm thick gold foil and soldered onto the center of the coaxial cable and the crystal to electrically couple to crystal 258 (note connector A shown in FIGS. 7B and 7C). The completed transducer (i.e., the combined lens 256/crystal 258 assembly) was placed into brass housing 252 and secured with epoxy (Hysol RE2039™ and HD3561™, from Loctite Corporation, Rocky Hill, Conn.). The crystal was air backed to ensure both cooling and minimum energy loss through the back-side. FIG. 7F is a photograph of the completed working model of transvaginal therapy probe 204.

As noted above, the purpose of using the tracking system discussed above to control the spatial orientation between a transvaginal therapy probe and a transabdominal imaging probe is to enable real-time, image-guided HIFU therapy. However, when the HIFU source is in operation, the high power levels saturate the ultrasound image probe receiver and circuitry, resulting in interference band patterns on the ultrasound image. To ensure that the image is interference-free where the focal point of the HIFU beam is to be visualized in the ultrasound image, the pulse gating method described in a related U.S. Pat. No. 6,425,867 (entitled "Noise-Free Real Time Ultrasonic Imaging of a Treatment Site Undergoing High Intensity Focused Ultrasound Therapy"), is used. As explained above and in this referenced patent, the HIFU source and the imaging ultrasound source are synchronized so that the interference area, proportional to the duty cycle, is spatially stable and moveable, as schematically illustrated in FIGS. 1B and 1C. It has been empirically determined that when the Sonosite C60 image probe is used in conjunction with transvaginal therapy probe 204, a 50% HIFU duty cycle is adequate for visualization of the HIFU focal point, resulting in a 65-70 degree window of visualization (out of a total ultrasound imaging window of 135 degrees), as shown in FIGS. 8A and 8B. An ultrasound image 270 in FIG. 8A includes a 67 degree window 272 of visualization that is noise free. Note that window 272 is disposed about 10 degrees from the left edge of the image, so that noise 274*a* obscures the first 10 degrees of ultrasound image 270, and noise 274*b* similarly obscures the last 58 degrees. An ultrasound image 276 in FIG. 8B also includes a 67 degree window of visualization that is noise free (i.e., a window 278). Note that window 278 is shifted relative to noise free window 272 of FIG. 8A. Thus, in FIG. 8B, window 278 is disposed about 40 degrees from the left edge, so that noise 280*a* obscures the first 40 degrees of ultrasound image 276, and noise 280*b* similarly obscures the last 28 degrees. Accordingly, the window of visualization can be shifted to ensure that the focal point of the HIFU beam can be visualized in the noise free portion of the ultrasound image. It should be understood that the window of visualization is dependent upon the image probe used and the imaging frame rate, and thus, other transabdominal imaging probes (or other frame rates) might result in a larger or smaller window of visualization.

FIG. 9 is a block diagram 284 that illustrates the functional elements used to empirically test the functionality of the concepts disclosed herein. The HIFU transducer incorporated into vaginal therapy probe 204 was driven with an RF amplifier 286 (Model ENI A150™, from MKS instruments, Andover, Mass.). A first waveform generator 294 (Model 33120A™, from Agilent Technologies, Palo Alto, Calif.) was used to provide the source signal. An RF power meter 288 (Model 4421™, Bird Electronics, Cleveland, Ohio) was connected between the amplifier and a matching network 290 to monitor electrical power output. A switch 292 was coupled between the output of waveform generator 294 and RF amplifier 286, to serve as an on/off switch. A timer 296 connected to the switch enabled HIFU exposure time to be measured. In order to provide synchronization (i.e., to enable visualization of the focal point of the HIFU beam by shifting noise introduced into an ultrasonic imaging by the HIFU beam, as described above), a second waveform generator 298 and a computer 300 were utilized. Computer 300 employed LabView™ software (National Instruments of Austin, Tex.) to control both waveform generators via a GPIB (General Purpose Interface Bus) connection. Waveform generator 298 was used to generate an excitation pulse. The excitation pulse triggered the output of waveform generator 298, which operated in burst mode, with a burst count corresponding to a 50% duty cycle. To ensure that the interference bands were spatially stable, the excitation pulse must always fall on the same image probe array element. The excitation pulse frequency (EPF) varied with imaging depth and was determined experimentally (by changing the EPF until the interference bands were spatially stable) and was then entered manually into the LabView™ control program. As described above, a tracking system (or a frame 200) can be used to ensure that the spatial orientation between transabdominal imaging probe 202 and transvaginal therapy probe 204 remains constant once it has been adjusted so that the focal point of the HIFU beam generated by transvaginal therapy probe 204 lies within the imaging plane generated by transabdominal imaging probe 202. The ultrasound image generated by transabdominal imaging probe 202 is viewed on a display 302.

Development of HIFU with Aluminum Lens

A study of the female pelvic anatomy was performed to determine the optimal geometry and dimensions for transvaginal therapy probe 204 and a frame which mechanically coupled the therapy transducer to an external imaging probe. Images from the Visible Human Project (National Library of Medicine, National Institute of Health), Gray's anatomy, 18 pelvic ultrasounds, and fibroid patient data files were used. Various configurations of transvaginal therapy probes and frames were modeled with SolidWorks™ (SolidWorks Corporation, Concord, Mass.) design software to determine optimal component sizes and geometry based on the above noted anatomical study.

The anatomical study revealed vaginal lengths ranging from 6-11 cm, uterine lengths of 5-9 cm, and uterine widths of 2-5 cm. A transvaginal therapy probe in accord with the present invention was designed to treat fibroids along the uterine cavity while placed in the vaginal fornix surrounding the cervix. Therefore, a HIFU focal length of 4 cm was determined to be optimal.

Numerical simulations indicated that an aluminum lens would be effective in focusing ultrasound energy. It was determined that a flat crystal and lens design (versus a spherical shell) would be used due to crystal availability, cost, and the possibility of using various lens geometries and focal configurations in the future. Aluminum has a low acoustic loss and a low characteristic acoustic impedance ($ZA_{Al}$=17.3 Mrayls) relative to most metals ($Z_{steel}$=46.7 Mrayls, $Z_{copper}$=42.5 Mrayls, and $Z_{titanium}$=27.0 Mrayls), making aluminum a suitable material for an acoustic lens in terms of minimizing attenuation and acting as an acoustic matching layer. Due to the high acoustic velocity of aluminum (6363 m/s) compared to water (1483 m/s), the curvature of the lens was small, and the maximum thickness of the lens was only 3 mm.

Based on the desired focal length and calculated attenuation losses in uterine tissue and fibroids, a PZT-8 crystal, 2.54 cm in diameter with a nominal frequency of 3.5 MHz, was selected to provide a sufficient focal gain. A 2.54 cm aluminum lens with a 4 cm focal length resulted in a maximum lens thickness at the outer edge of 3 mm and an f-number of 1.57. Although side lobes were noticed in the Schlieren imaging, they were quantified as relatively small (approximately 20 dB) compared to peak focal intensities on the field map. Such side lobes may be a result of re-radiation, reflections, and shear wave conversion within the lens and at the crystal-epoxy-lens interface, since they were apparent in another HIFU transducer design at similar power levels, which also involved the use of a PZT crystal bonded to an aluminum waveguide. Although the epoxy used to bond the aluminum lens to the PZT was nonconductive, roughness on both lens and PZT surfaces at the microscopic level allowed for areas of direct contact and thus, conduction while the two surfaces were bonded under 400 kPa of bonding pressure.

The maximum diameter of the brass housing for the PZT crystal and aluminum lens combination was 28.5 mm, which is sufficiently small to readily fit into the vagina. While optimizing the HIFU transducer size to fit in the vagina, it was ensured that the aperture size chosen was able to deliver sufficient power to the treatment site. A transvaginal versus transabdominal treatment approach was chosen since it provided the shortest acoustic path to the uterus (approximately 0.5 cm from the vaginal fornix to the uterus, versus approximately 4 cm via the abdomen, depending on bladder size). The large attenuation loss associated with the abdominal path (losses in skin, fat, abdominal wall, and bladder fluid) were thus eliminated using the transvaginal approach.

As noted above, a piezoelectric ceramic (PZT-8) crystal was selected to generate the HIFU, and an aluminum lens was selected to focus the HIFU beam. The curvature of the aluminum lens was calculated such that waves from each point on the surface of the crystal would pass through the lens and arrive at the focus at the same time. This focusing effect is schematically illustrated in FIG. 10A, for a lens focusing at 4 cm, where $t_{1i}+t_{2i}=t_0$ and i represents a point location on the crystal. The variables used in Equation 1 (below) that govern the shape of the lens are indicated in FIG. 10A. The coordinates of the lens curvature fit the quadratic relation in Equation (1), where ($x_i$, $y_i$) are the coordinates of the lens curvature, $x_f$ is the focal length, and $c_1$ and $c_2$ are the measured acoustic velocities in the aluminum lens (6363 m/s) and in water (1483 m/s), respectively:

$$x_i^2\left(1-\frac{c_2^2}{c_1^2}\right)+x_i\left(2x_f\frac{c_2}{c_1}-2x_f\right)+(y_i^2)=0 \quad (1)$$

A computer simulation was used to determine the effectiveness of the aluminum lens in focusing ultrasound. Wave 2000 Pro™ (Cyberlogic, New York, N.Y.), a program for studying two-dimensional (2D) wave propagation fields, was used to compute the finite difference solution to the 2D wave equation in both spatial and temporal domains. Shear and compression coupling and viscous loss attenuation were included in the algorithm. The geometry, material properties, and ultrasound sources and receivers were modeled. The geometry, shown in FIG. 10B, consisted of a simplified model of the transducer: an air-backed PZT-8 crystal bonded to an aluminum lens with an epoxy bond layer. Source pulses of 3 ms and continuous wave sources were modeled in a simulated treatment path consisting of water and uterine tissue. Simulated ultrasound point receivers for particle displacement measurement were located at the focus and at various points along the focal axes (1, 2, 5, 10, and 20 mm to the left and right of the focus, and 1, 2, and 5 mm above and below the focus), as depicted in FIG. 10B. The time duration for each simulation was set at 45 ms, allowing the wave to propagate a few centimeters past the focus. Normalized particle displacement data were extracted from the simulations. An aluminum lens developed using the above described model was machined using a CNC lathe. Fabrication of the transvaginal therapy probe is described above.

Wave 2000 Pro™ computer simulations demonstrated the feasibility of the aluminum lens design in focusing ultrasound. A propagating 3 ms pulse for a 3.5 MHz sinusoidal ultrasound source focusing at 4 cm through an aluminum lens at various times was simulated. The normalized peak particle displacement amplitudes determined from simulation receiver data at various locations were also calculated. FIG. 11A is a composite of images extracted from the Wave 2000 Pro™ simulation, showing a 3.5 MHz, 3 μs sinusoidal pulse wave at four different times (7 μs, 2 μs, 30 μs, and 37 μs). The approximate time when the wave front reached the focus was at 30 μs. The program created a black background during the simulation for contrast, and the various minima and maxima of the wave are shown in white, with areas that remain black showing locations where the waveform has zero amplitude.

FIG. 11B graphically illustrates the peak normalized particle displacements collected from the Wave 2000 Pro™ simulation receiver data. Since acoustic pressures are proportional to particle displacements, the half-pressure maximum focal dimensions can be estimated as being about 10 mm in length by about 1 mm in width, as indicated in FIG. 11B.

The actual acoustic beam pattern provided by the aluminum lens and PZT-8 crystal fabricated as described above was initially determined with a Schlieren imaging system at three different acoustic power levels, including: 10, 30, and 60 W (continuous wave). FIG. 12A illustrates a composite of the Schlieren images obtained at the above noted power levels. Side lobes 304 are indicated at power levels around 60 W.

FIG. 12B graphically illustrates an acoustic field map created using data collected with a PVDF needle hydrophone (from NTR Systems Inc., Seattle, Wash.) during empirical testing of the transducer generated using the PZT-8 crystal and the aluminum lens described above. Technically, the act of transduction of energy (from electrical to a acoustical) is performed by the crystal, however, those of ordinary skill in the art will readily recognize that the term transducer is often used to refer not only to the crystal itself, but also to a crystal combined with a lens. The hydrophone was 0.5 mm in diameter and was moved using stepper motors. The acoustic power output was determined using a radiation force balance technique. The field map shows the HIFU focus at a half-pressure maximum (26 dB) with measured dimensions of about 11 mm in length and about 1.2 mm in width, which are similar to the values predicted with the computer model. Side lobes can be seen but were at values below approximately 20 dB. The acoustic power output was determined using a radiation force balance technique.

Results obtained from the radiation force balance are shown in FIG. 13. This plot shows the correlation between electrical power and acoustic power, as well as the efficiency at the power levels tested. The average efficiency between 0 and 150 W of acoustic power was determined to be 58%, +/−2% (n=9 power levels).

In-vitro testing of the PZT-8/aluminum lens transducer in gel and animal tissue verified the functionality of the design. A transparent tissue-mimicking gel phantom was used to determine if lesions can be formed at target locations, if these lesions can be visualized using ultrasound, and if the water balloon affects the formation of lesions. The thermally sensitive gel employed was based on a combination of bovine serum albumin and polyacrylamide, and changes from transparent to opaque when treated with HIFU. The attenuation of the gel was measured to be 0.012+/−0.002 NP/cm/MHz (n=30). Gel blocks (6.5×5.5×5.5 cm) were placed in a plastic holder, submerged, and anchored in a plastic tank filled with degassed distilled water at room temperature. The transvaginal therapy probe described above (i.e., transvaginal therapy probe 204) was suspended in the water tank using a metal clamp and positioned such that the focal region of the HIFU transducer was within the gel block, and the image probe was capable of visualizing the treatment.

Three treatment scenarios were investigated, as follows: (1) the transducer was placed directly on the gel surface; (2) the transducer was placed 1.2 cm away from the gel surface and separated therefrom by a water-filled condom; and, (3) the transducer was placed 1.2 cm away from the gel surface without a water-filled condom intervening. All lesions were produced using 46 W of acoustic power for 5 seconds at 50% duty cycle. The ultrasound imaging unit (Sonosite™, from Sonosite Inc., Bothell, Wash.) was connected to a digital video recorder and ultrasound images were recorded during treatment. A digital camera, mounted on a tripod, was used to photograph lesions formed in the transparent gel. Lesion dimensions were measured using these photographs within Adobe Photoshop™ (Adobe Systems Incorporated, Seattle, Wash.).

TABLE I

Measured dimensions for HIFU lesions in gel with and without water stand-off.

| Treatment scenario (n = 10 for each) | In situ focal intensity (W/cm$^2$) | Lesion length (mm) | Lesion width (mm) | Ultrasound visualization |
|---|---|---|---|---|
| Transducer directly on gel | 1410 | 11.2 +/− 0.8 | 2.2 +/− 0.6 | 10/10 |
| 1.2 cm separation; no condom | 1590 | 13.5 +/− 1.1 | 2.6 +/− 0.7 | 10/10 |
| 1.2 cm separation; with condom | 1590[1] | 13.3 +/− 0.9 | 2.5 +/− 0.8 | 10/10 |

[1]Attenuation of the 0.07 mm thin condom (Trojan Brand Non-Lubricated, CWI Carter Products Div., New York, NY) was assumed to be zero.

FIG. 14A illustrates a composite image including both a photograph 320 of the distal end of transvaginal therapy probe 204 coupled to a gel phantom, as well as an ultrasound image 322 of the distal end of transvaginal therapy probe 204 coupled to the gel phantom. In both the photograph and the ultrasound image, brass housing 252, expandable member 244, and aluminum lens 256 can be observed. Note that in ultrasound image 322, degassed water **244*a* used to inflate the latex condom (i.e., expandable member 244) can be identified. FIG. 14B is a composite image including a similar photograph and ultrasound image, taken after HIFU therapy. A lesion 326 can be observed in both a photograph 324 and in an ultrasound image 328. These images depict a treatment scenario wherein the transducer and gel are separated by 1.2 cm of water contained within a water-filled condom. The HIFU transducer and the water-filled condom are clearly seen in the ultrasound images (i.e., ultrasound images 322 and 328). Lesion 326, which was formed by HIFU, can be clearly seen in photograph 324 as a white opaque spot in the transparent gel, and as a bright hyperechoic spot in ultrasound image 328**. The lesion appears to be tadpole-shaped, indicative of the presence of cavitation mechanisms during lesion formation. The measured lesion dimensions for three different treatment scenarios (no condom/no separation, 1.2 cm separation with no condom, and 1.2 cm separation with liquid-filled condom), are shown in Table I. At 46 W of acoustic power and 50% duty cycle, the focal intensity was 1400 W/cm$^2$ with the transducer on the surface of the gel and 1590 W/cm$^2$ with the transducer and gel separated by 1.2 cm of water. A two-sample, two-tailed test indicated no statistically significant difference between lesions created both with the water-filled condom stand-off, and without ($P<0.05$). Lesion size was proportional to HIFU focal intensity. All lesions were visualized with ultrasound.

The ability for the device to produce and visualize lesions in tissue was then determined using fresh turkey breasts. The turkey breast samples used in the experiment were stabilized at 25° C. prior to treatment and had a measured attenuation of 0.096+/−0.002 NP/cm/MHz. Attempts were made to create lesions perpendicular to the muscle fibers at selected HIFU focal intensities between 500 and 4000 W/cm$^2$, at 5 and 10 seconds of exposure, and 50% duty cycle. The spatial and temporal averaged frequency dependent HIFU focal intensity ISATA was determined to be:

$$I_{SATA} = \frac{P_A * DC}{A}(e^{-2\alpha_T x_T})(e^{-2\alpha_w x_w}) \quad (2)$$

where $P_A$ is acoustic power, DC is duty cycle, A is the half pressure maximum (23 dB) focal area, $\alpha_T$ and $\alpha_W$ are the respective attenuation coefficients of tissue and water, and $x_T$ and $x_W$ are the depths in tissue and water, respectively. The tissue was dissected at the lesion location and lesion length and width were measured using digital calipers. It was noted whether or not each lesion was visualized using ultrasound imaging during treatment.

Such HIFU created lesions, and the ultrasound visualization of treatment in a turkey breast using transvaginal therapy probe 204 are shown in FIGS. 15A and 15B. FIG. 15A is a photograph 330 of a dissected turkey breast, which includes lesions induced by HIFU therapy. A lesion 332*a* was generated using a power level of 3800 W/cm$^2$ applied for 5 seconds; a lesion 332*b* was generated using a power level of 1600 W/cm$^2$ applied for 10 seconds; a lesion 332*c* was generated using a power level of 2200 W/cm$^2$ applied for 5 seconds; and a lesion 332*d* was generated using a power level of 800 W/cm$^2$ applied for 10 seconds. Normal turkey breast (i.e., no lesions) is generally indicated by an arrow 334.

FIG. 15B is a composite image of a turkey breast and a HIFU therapy probe, including an ultrasound image 336*a*, generated before the application of the HIFU beam, and an ultrasound image 336*b*, generated after the application of the HIFU beam. Each ultrasound image includes a turkey breast 335 and the distal portion of transvaginal therapy probe 204, including aluminum lens 256. A lesion 338 is clearly visible after the HIFU therapy in ultrasound image 336*b*.

As indicated below in Table II, visualization was successfully achieved 100% of the time at a power level of 3600 W/cm$^2$, and 70% of the time at a power level of 1200 W/cm$^2$.

TABLE II

Measured dimensions for HIFU lesions in a turkey breast at two intensity levels.

| In situ focal intensity (W/cm$^2$) | Lesion length (mm) | Lesion width (mm) | Number of samples | Ultrasound visualization |
|---|---|---|---|---|
| 1200 | 10.6 +/− 3.1 | 2.1 +/− 0.3 | 10 | 7/10 |
| 3600 | 21.6 +/− 1.1 | 5.1 +/− 0.3 | 10 | 10/10 |

Once the effectiveness of transvaginal therapy probe 204 was empirically tested using gel phantoms and turkey breasts as described above, the ergonomics of transvaginal therapy probe 204, the frame, and transabdominal imaging probe 202 were tested in six healthy human volunteers, in accordance with a human subjects research protocol approved at the University of Washington. The volunteers were neither pregnant nor had undergone a hysterectomy. A sterile condom (to implement expandable member 244) was secured to the distal end of transvaginal therapy probe 204, lubricated, and filled with water prior to insertion into the vagina. Once the transvaginal therapy probe was inside the vagina, the transabdominal imaging probe was positioned to visualize pelvic structures and the transvaginal therapy probe. Uterus dimensions were measured on the ultrasound image. Once visualization was possible, the transvaginal therapy probe was mechanically moved and positioned to hypothetically treat various areas of the uterus. The amount of transducer movement was quantified using a ruler drawn onto the transvaginal therapy probe and by observing the relative position of the transvaginal therapy probe in the ultrasound image. The distances from the transducer in the transvaginal therapy probe to the fundus, mid-uterus, and cervix were measured to determine the potential treatable area. Water was injected and removed from the condom to determine the feasibility of using a water-filled condom as a stand-off.

TABLE III

Human volunteer statistics and uterus measurements.

| Volunteer | Age (years) | Body mass index | Uterus orientation[d] | Uterus length (cm) | Uterus width (cm) | Distance to cervix[e] (cm) | Distance to mid uterus (cm) | Distance to fundus |
|---|---|---|---|---|---|---|---|---|
| 1 | 26 | 20.4 | A | 6.15 | 3.42 | 1.88 | 2.69 | 3.92 |
| 2 | 27 | 22.0 | A | 5.90 | 3.21 | 1.83 | 2.52 | 3.87 |
| 3[a] | 49 | 22.9 | A | 8.49 | 4.63 | 1.92 | 3.18 | 4.33 |
| 4 | 23 | 22.7 | A | 7.21 | 3.90 | 1.98 | 3.21 | 3.00 |
| 5 | 32 | 29.9 | M | 7.26 | 3.33 | 2.17 | 3.50 | 4.78 |
| 6[b] | 42 | 24.6 | M | 11.7 | 8.03 | 3.61 | 5.64 | 5.44 |
| Mean | 33.17 | 23.75 | | 7.79 | 4.42 | 2.23 | 3.46 | 4.22 |
| St Dev[c] | 12.23 | 3.31 | | 2.13 | 1.84 | 0.69 | 1.13 | 0.84 |

[a]Volunteer had children.

[b]Volunteer had a fibroid located in the fundus.

[c]Standard deviation.

[d]A = aniflexed; M = midline

[e]Distance measure from the aluminum lens of the transvaginal therapy probe.

Volunteer statistics and uteri measurements are shown in Table III. The volunteers ranged in age between 23 and 49 years, and in body mass index (weight in kilograms divided by the square of height in meters) between 20.4 and 29.9. One volunteer had previously given birth, and one volunteer had a fibroid located in the fundus. Four volunteers had aniflexed uteri (a condition in which the uterus is pointed towards the abdomen) and two had midline uteri. Uteri length ranged between 5.90 and 8.49 cm and width ranged between 3.21 and 4.63 cm, excluding the volunteer with a fibroid, wherein the total uterus length and width, including the fibroid, were 11.7 cm and 8.03 cm, respectively. As shown in Table III, if treatment was to be administered, the 4 cm focal length of transvaginal therapy probe 204 would have been sufficient to treat fibroids located in the cervix and mid-uterus of all volunteers (an average distance of 2.23 cm and 3.46 cm, respectively).

According to the survey completed by the volunteers after the study, entrance into the vagina was comfortable if lubrication was used and sufficient water was inside the condom to act as a cushion between the vaginal wall and the HIFU transducer (i.e., the distal end of transvaginal therapy probe 204). No discomfort was experienced while the probe was in the vagina and while the probe was being removed from the vagina.

The above-noted study provides a feasibility assessment for image guided HIFU therapy using transvaginal therapy probe 204, transabdominal imaging probe 202, and a frame (or the free hand registration system discussed above), for treating uterine fibroid tumors. The transvaginal HIFU transducer (crystal 258 and lens 256) has the potential to treat fibroids through the width of the uterus when placed in the vaginal fornix. In designing transvaginal therapy probe 204 and frames, anatomical constraints of the female pelvic structures were taken into account. The 28.5 mm diameter transducer head was sufficiently small to fit into the vagina. While optimizing the HIFU transducer size to fit in the vagina, it was ensured that the aperture size chosen was able to deliver sufficient power to the treatment site. Placement of the device in human volunteers demonstrated successful visualization of the HIFU transducer and the uterus. The water-filled condom and the transducer lens surface were easily seen in the ultrasound images. Since the transducer had a fixed focal length of 4 cm, a potential treatment location can be determined on the ultrasound image at a distance of 4 cm away from the transducer lens. Mechanical movement of the HIFU transducer was possible once in the vagina and provided access to a potential treatment area that spanned from the cervix to the fundus of the uterus. The ergonomic study indicated that the insertion, maneuvering, and removal of the probe were comfortable for the volunteers. The ergonomic study also indicated that a HIFU transducer with a fixed focal length of 4 cm is capable of treating fibroids located in the cervix and mid-uterus area in most women with aniflexed and midline uteri. However, fibroids located in the fundus of midline uteri and uteri of women who have previously given birth (i.e., within larger uteri) may require a longer focal length or treatment using transabdominal HIFU. Since an individual lesion is not large enough to cover a fibroid, multiple lesions would be required for fibroid treatment. Therefore, large fibroids may require a long treatment time or not be suitable for HIFU treatment. The target fibroids for this treatment modality are submucosal fibroids. Submucosal fibroids are located under the endometrium of the uterus, accessible with a 4 cm focal length, and represent the most symptomatic type of fibroids. They are often smaller in size than intramural or subserosal fibroids, making them more suitable for HIFU treatment.

The two methods currently used for HIFU therapy visualization are magnetic resonance imaging (MRI) and ultrasound. Both can be used to image fibroids. In an ultrasound image, fibroids often appear hypoechoic (as darkened regions). The Sonosite™ ultrasound unit was chosen for this study, since it allowed for image guidance and was portable and inexpensive compared to larger ultrasound units and MRI. As shown in this study, transabdominal ultrasound image-guidance provides real-time imaging of the HIFU treatment. MRI provides imaging visualization of the HIFU thermal field and coagulated region within five seconds of treatment, and is thus not a real-time visualization. With ultrasound imaging, treating tumors with multiple lesions is facilitated, since the HIFU-induced hyperechoic spot remains after treatment for a duration dependent on the exposure intensity. Furthermore, treatment dosimetry, and not just treatment location, can be determined, since the hyperechoic spot size is proportional to the size of the lesion created. It was noted in the turkey breast that hyperechoic spots only appear above a specific intensity threshold (>1250 W/cm$^2$). Therefore, there is a possibility that exposures at lower doses may result in a physical lesion that cannot be visualized. This apparent intensity threshold will need to be determined in human uterus samples. The mechanisms behind the formation of hyperechoic spots are not well understood. However, it can be inferred from the in vitro testing in this study that the hyperechoic region during HIFU treatment is due to a combination of tissue properties changing due to tissue necrosis, cavitation activity, and gross deformation resulting in voids within the tissue. It is desirable to determine the location of the potential area of lesion formation prior to treatment. An electronic method using position transducers for targeting is currently being developed to enable the treatment area to be visualized without relying on the hyperechoic spot. Furthermore, computer-aided treatments that keep track of the treated areas on the ultrasound image may be employed in the future to compensate for any decrease in echogenicity in the hyperechoic spot.

The in vitro testing in gel demonstrated the feasibility of using the transvaginal HIFU transducer to form lesions. The testing on a turkey breast indicated a HIFU dose dependent lesion formation in tissue. It was shown that increasing the intensity or exposure time can increase lesion size. It was also shown that the intensity required for the onset of lesion formation was lower for a 10 second treatment duration (about 760 W/cm$^2$) versus a 5 second treatment duration (about 1170 W/cm$^2$). Lower HIFU intensities (ranging from about 760 W/cm$^2$ to about 2800 W/cm$^2$) resulted in cigar-shaped lesions that have been characterized as due to purely thermal effects. Higher HIFU intensities (i.e., above about 2800 W/cm$^2$) resulted in tadpole-shaped lesions, with a distinct head and tail that were characterized as lesions with a significant contribution from inertial cavitation activity and vaporization.

The thermal and cavitation effects at the focus and surrounding tissue will be subject to further investigation to determine optimal treatment parameters for uterine fibroids. Effective acoustic coupling from the HIFU transducer to the tissue of interest is crucial for successful treatment. Water is an effective acoustic coupler, due to its similarity in acoustic impedance to tissue. Since there was potential for air to be trapped between the transducer and the vaginal wall when the device was used in vivo, a method of acoustic coupling was devised using a water-filled condom that eliminated pockets of air, as described in further detail below. Testing of the device with the gel phantom revealed that the condom essentially acted as an acoustically transparent thin membrane that did not statistically affect the size of lesions. The condom further provided a sterile protective membrane. Focal depth control was possible by selectively inflating and deflating the condom with water and thus varying the distance between the transducer and the uterus, effectively varying the treatment location. Water circulation within the condom provides cooling to the transducer while in operation. Factors such as blood perfusion, air entrapment, and nonlinear effects of HIFU treatment need to be taken into consideration and may be the subjects of a future investigation.

Still another aspect of the present invention is directed to a method of verifying a quality of the coupling between an ultrasound therapy probe and a tissue interface. FIG. 17A schematically illustrates a transvaginal therapy probe 204*b* coupled to a tissue mass 406. Transvaginal therapy probe 204*b* is substantially similar to transvaginal therapy probe 204 described above, however transvaginal therapy probe 204*b* further includes a liquid flushing line 251, whose purpose will be described in greater detail below. Transvaginal therapy probe 204*b* similarly includes housing 252 disposed at the distal end of transvaginal therapy probe 204*b*. Housing 252 encapsulates the therapy transducer. Expandable member 244 (i.e., a latex condom) is attached to housing 252, and filled with liquid to facilitate coupling transvaginal therapy probe 204*b* to tissue mass 406. With respect to transvaginal therapy probe 204*b*, tissue mass 406 generally will be within the uterus. It should be understood that the method of verifying a quality of the coupling between an ultrasound therapy probe and a tissue interface is not limited to use with any specific therapy probe, or any specific tissue mass. Thus, the inclusion of transvaginal therapy probe 204*b* in FIG. 17A is intended to be exemplary, rather than limiting of the present invention.

A plurality of air bubbles 408 can be seen between expandable member 244 and tissue mass 406. The presence of such air bubbles at the interface between the therapy probe and the tissue mass will negatively affect the transmission of the HIFU beam through the interface, which will result in a degradation of the therapy being performed, because such air bubbles interfere with the propagation of the HIFU beam from the therapy transducer to the focal point/target area. The presence of air bubbles will reduce the amount of energy transmitted by the HIFU beam. Generally such air bubbles are most likely to be outside of the expandable member, in between the expandable measure member and the tissue mass. The liquid used to inflate the expandable member is preferably treated to remove any air bubbles in the liquid (i.e. the liquid is degassed), so it is more likely that air bubbles would become trapped outside of the expandable member, as opposed to inside the expandable member. To dislodge air bubbles trapped between the expandable member and the tissue interface, transvaginal therapy probe 204*b* can be manipulated such that the expandable member moves relative to the tissue mass, thereby dislodging any air bubbles. An additional technique that can be used to dislodge air bubbles would be to inflate or deflate the expandable member. Liquid flushing line 251 can be used to flush the interface with a rinse liquid to remove the air bubbles, as indicated by an arrow 253. If the air bubbles have formed inside of the expandable membrane, the liquid in the expandable membrane can be replaced with degassed liquid. Examination of the positions of the air bubbles relative to the interface and the expandable membrane will indicate whether the air bubbles are located in the liquid filling the membrane, or between the membrane and the tissue, so an appropriate corrective action can be taken.

FIG. 16 shows a flowchart 390 that indicates the sequence of logical steps to determine whether such air bubbles are present. In a block 392 a therapy probe is introduced into a body cavity, such as the vagina. While most often, therapy probes in accord with the present invention will be used within the body cavities, it should be understood that therapy probes can also be used in external applications, so that the therapy probe/tissue interface is outside the patient's body. Thus, it should be understood that the present invention is not limited to detecting air bubbles at tissue interfaces within a body cavity. In a block 394, the expandable member (such as a balloon or a latex condom) is inflated with a liquid (such as water or saline solution) that supports propagation of the HIFU beam. In some applications, the expandable member may be at least partially inflated with the liquid before the therapy probe is introduced into a body cavity, to provide a cushioning effect. In a block 395, the therapy probe is properly positioned relative to the tissue interface, so that the expandable member contacts the tissue interface and slightly deforms, thereby efficiently coupling the therapy probe to the tissue. In a block 396, the quality of the coupling between the expandable member and the tissue interface is evaluated, to determine if there are any air bubbles within the liquid. In a decision block 398, it is determined whether any such bubbles are present. If so, then in a block 400 appropriate action is taken to dislodge the air bubbles. Techniques for dislodging air bubbles include repositioning the therapy probe to dislodge the air bubbles, inflating or deflating the liquid-filled membrane to dislodge the air bubbles, and flushing the interface with an irrigation liquid to dislodge the air bubbles. An additional check is then made to determine whether any more air bubbles are present, after the therapy probe is repositioned. If, in decision block 398, it is determined that no such air bubbles are present, therapy is performed, as indicated in a block 402.

FIG. 17B schematically illustrates transvaginal therapy probe 204*b*, including expandable member 244, coupled to tissue mass 406, such that no air bubbles are present at the tissue interface. Once administration of the therapy is completed, the probe is removed from the body cavity, as indicated in a block 404 (of FIG. 16).

As noted in the details of block 396 (shown in FIG. 16), several different techniques can be used to check for the presence of air bubbles. A hysterscope can be used to optically check for the presence of air bubbles, as indicated in a block 396*a*. FIG. 18 is a photograph of a commercially available hysterscope 416. Those of ordinary skill in the art will recognize that a hysterscope is a relatively common gynecological instrument. Due to its widespread availability, most medical offices treating gynecological disorders will have access to such an instrument. Due to the small size of the hysterscope, it is quite feasible for both a transvaginal therapy probe and a hysterscope to be accommodated in the vaginal canal at the same time. The hysterscope provides real-time images, and can be manipulated so that the clinician can visually check for the presence of any air bubbles at the interface between the tissue mass and the therapy probe. If the clinician observes the presence of any air bubbles at the tissue/transvaginal therapy probe interface, the clinician can manipulate the transvaginal therapy probe to dislodge any air bubbles that were observed. While a rigid hysterscope is illustrated, it should be understood that flexible hysterscopes, or other flexible imaging devices, can be similarly employed for this purpose.

The therapy probe itself can also be used to check for the presence of air bubbles, when the therapy probe is energized at a low-power level, as indicated in a block 396*b*. When energized at a low-power level, the HIFU transducer transmits a low-power pulse. The reflected pulse is detected and analyzed. Either a therapy probe or an imaging probe can be used to detect the reflected pulse. If the intensity of the reflected pulse is higher than a predefined threshold level, it can be concluded that there are air bubbles disposed at the interface, and those air bubbles are responsible for the reflected pulse. For specific applications and equipment, the threshold level can be determined empirically. Otherwise, a reasonable threshold level would be a 15-20% increase in a background level. The HIFU beam is energized at a low-power setting to check for air bubbles, which ensures that tissue necrosis does not occur until a satisfactory coupling of the therapy probe to the tissue mass has been achieved and the HIFU beam is energized at a substantially higher intensity.

Still another technique for determining whether any air bubbles are present at the tissue/therapy probe interface involves using an ultrasound imaging probe, as indicated in a block 396*c*. The ultrasound imaging probe can either be integrated onto the therapy probe, or a separate ultrasound imaging probe can be employed. Any air bubbles present at the tissue/therapy probe interface can be readily identified, because they will appear as bright spots in the ultrasound image. If an ultrasound imaging probe is used to determine whether any air bubbles are present, the therapy probe does not need to be energized at all during the check for air bubbles.

Another aspect of the present invention is directed to still another embodiment of a transvaginal therapy probe 410 that includes a generally spoon-shaped therapy transducer 412, a schematic representation of which is provided in FIG. 19A. FIG. 19B is a schematic representation of the distal end of transvaginal therapy probe 410, clearly showing generally spoon-shaped therapy transducer 412. FIG. 19C schematically illustrates transvaginal therapy probe 410 removably coupled to a commercially available transvaginal imaging probe 120, to enable visualization of the focal point of the HIFU beam during therapy, generally as described above. As indicated in FIG. 19C, the distal end of hysterscope 416 is also removably coupled to the transvaginal therapy probe and the transvaginal imaging probe. A hook and loop fastener 414 is employed to removably couple the elements together. Those of ordinary skill in the art will readily recognize that other types of fasteners or mounting system can be similarly employed to removably couple the elements together. As noted above, it should be understood that in addition to hysterscope 416, other imaging devices can be used, such as optical fiber-based flexible scopes. The development of digital imaging devices is producing increasingly smaller devices, and if sufficiently small digital imaging devices become available, digital imaging devices can also be employed for this purpose.

FIG. 19D schematically illustrates generally spoon-shaped transducer 412 included in transvaginal therapy probe 410, clearly showing the plurality of different emitter elements that are included therein. Generally spoon-shaped transducer 412 includes 11 discrete emitter elements, all equal in area, each element being separated from its neighbors by 0.3 mm. Six of the emitter elements have complete annuli, and five emitter elements have truncated annuli. The overall transducer dimensions are about 35 mm×60 mm. Generally spoon-shaped transducer 412 is magnetic resonance image (MRI) compatible, has a center frequency of 3 MHz, a focal length of 3-6 cm, a geometric focus of 5 cm, and a maximum focal intensity of 3000 W/cm$^2$. Techniques for ensuring that a transducer is compatible with MRI are disclosed by Hynynen K, Darkazanli A, Schenck J F et al. MRI-guided noninvasive ultrasound surgery. *Med.Phys*., vol. 20, pp. 107-115, 1993.

Still another aspect of the present invention is directed to an integration of a hysterscope (to optically determine whether air bubbles exist at a tissue interface), a transvaginal imaging probe, and a transvaginal therapy probe into a single compact instrument that is capable of optically determining whether any air bubbles exist at the instrument/tissue interface, and which enables visualization of the focal point of the HIFU beam during therapy. In a related embodiment, an optical imaging element is incorporated into a transvaginal therapy probe. Such an imaging element can be based on a hysterscope, as described above, or based on an optical fiber, as well as sufficiently compact digital imaging electronics (i.e. the imaging components in a digital camera or a digital video camera). Thus, in reference to FIG. 19C, it should be understood that reference number 416 could be implemented using a rigid hysterscope, a flexible optical fiber, or compact digital imaging electronics.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A probe for administering ultrasound therapy to a treatment site within a patient's body, wherein a tissue mass is disposed between the probe and the treatment site, the probe comprising:

an elongate supporting structure, having a distal end and a proximal end, wherein the elongate supporting structure comprises a section at the proximal cud configured to be grasped and manipulated by a clinician to at least initially position the distal end of the elongate supporting structure at a desired location generally adjacent to the tissue mass;

a high intensity focused ultrasound (HIFU) transducer disposed at the distal end of the elongate supporting structure, wherein the HIFU transducer comprises an aperture through which HIFU waves are transmitted, the aperture being of a sufficient size to transmit therapeutic HIFU waves such that the therapeutic HIFU waves have sufficient intensity remaining upon reaching the treatment site after being attenuated by the passage of the therapeutic HIFU waves through the tissue mass to achieve a desired therapeutic effect without substantially damaging a portion of the tissue mass through which the therapeutic HIFU waves initially propagate toward the treatment site;

a light based imaging element directed generally toward an interface between as flexible membrane substantially encapsulating the distal end of the elongate supporting structure and the tissue mass, the light based imaging element being configured to determine whether air bubbles are present at the interface, wherein the flexible membrane is configured to be inflated with a liquid to as desired extent when the distal end of the elongate supporting structure is disposed adjacent to the tissue mass such that the flexible membrane will substantially conform to the tissue mass and, thereby ultrasonically couple the HIFU transducer to the tissue mass and means for dislodging air bubbles at the interface.

2. The probe of claim 1 wherein the imaging element comprises an optical imaging element.

3. The probe of claim 2 wherein the optical imaging element comprises an optical fiber.

4. The probe of claim 1 wherein the imaging element comprises a digital imaging device.

5. The probe of claim 1 wherein the HIFU transducer comprises an air backed piezoceramic crystal coupled to an aluminum lens element.

6. The probe of claim 1 wherein the HIFU transducer comprises a generally spooned-shaped transducer including a plurality of discrete emitter elements, each emitter element having a substantially equivalent area.

7. The probe of claim 1 wherein the means for dislodging air bubbles at the interface comprises a liquid flush line configured to discharge an irrigation liquid proximate the distal end of the elongate supporting structure to dislodge air bubbles proximate the distal end of the elongate supporting structure that could interfere with the HIFU waves transmitted by the HIFU transducer.

8. The probe of claim 1 wherein the means for dislodging air bubbles comprises a fluid line in communication with the interface between the flexible membrane and the distal end of the elongate supporting structure the fluid line being configured to selectively inflate and/or deflate the flexible membrane with the liquid.

9. The probe of claim 1 wherein the means for dislodging air bubbles comprises means for dislodging air bubbles at the interface between the flexible membrane and the tissue mass.

10. A probe for administering ultrasound therapy to a treatment site within a patient's body, wherein a tissue mass is disposed between the probe and the treatment site, the probe comprising:

(a) an elongate supporting structure having a distal end and a proximal end, wherein the elongate supporting structure comprises a section at the proximal end configured to be grasped and manipulated by a clinician to at least initially position the distal end of the elongate supporting structure at a desired location generally adjacent to the tissue mass;

(b) a high intensity focused ultrasound (HIFU) transducer disposed at the distal end of the elongate supporting structure, wherein the HIFU transducer comprises an aperture through which HIFU waves are transmitted, the aperture being of a sufficient size to transmit therapeutic HIFU waves such that the therapeutic HIFU waves have sufficient intensity remaining upon reaching the treatment site after being attenuated by their passage through the tissue mass to achieve a desired therapeutic effect without substantially damaging a portion of the tissue mass through which the therapeutic HIFU waves initially propagate toward the treatment site, the HIFU transducer further comprising at least one of the following an air backed piezoceramic crystal coupled to an aluminum lens element, or a generally spooned-shaped transducer comprising a plurality of discrete emitter elements, each emitter element having a substantially equivalent area; and (c) means for dislodging air bubbles between the HIFU transducer and the tissue mass.

11. The probe of claim 10, further comprising a light based imaging element directed generally toward an interface between a flexible membrane substantially encapsulating the distal end of the elongate supporting structure and the tissue mass to determine whether air bubbles are present at the interface, wherein the flexible membrane is configured to be inflated with a liquid to a desired extent when the distal end of the elongate supporting structure is disposed adjacent to the tissue mass such that the flexible membrane will substantially conform to the tissue mass and thereby ultrasonically couple the HIFU transducer to the tissue mass.

12. The probe of claim 10 wherein the imaging element comprises an optical fiber.

13. The probe of claim 10 wherein the imaging element comprises a digital imaging device.

14. The probe of claim 10, further comprising a hysterscope proximate the distal end of the elongate support member, wherein the hysterscope is configured to provide real-time images to visually check for the presence of air bubbles between the HIFU transducer and the tissue mass.

15. The probe of claim 10, further comprising means for emitting, a non-therapeutic level of ultrasound to detect air bubbles proximate the distal end of the elongate supporting structure.

16. The probe of claim 15 wherein the means for emitting, the non-therapeutic level of ultrasound to detect air bubbles comprises the HIFU transducer.

17. The probe of claim 10 wherein the means is dislodging air bubbles comprises a flushing line configured to flush a rinse liquid proximate the distal end of the elongate supporting structure to dislodge air bubbles proximate the distal end of the elongate supporting structure.

18. The robe of claim 10 wherein the means for dislodging air bubbles comprises a fluid line configured to inflate and/or deflate a flexible membrane over the distal end of the elongate supporting structure.

* * * * *